(12) United States Patent
Chou et al.

(10) Patent No.: US 11,523,752 B2
(45) Date of Patent: Dec. 13, 2022

(54) ASSAY FOR VAPOR CONDENSATES

(71) Applicant: Essenlix Corporation, Monmouth Junction, NJ (US)

(72) Inventors: Stephen Y. Chou, Princeton, NJ (US); Wei Ding, East Windsor, NJ (US); Yufan Zhang, Monmouth Junction, NJ (US); Ji Qi, Hillsborough, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 115 days.

(21) Appl. No.: 16/485,126

(22) PCT Filed: Feb. 16, 2018

(86) PCT No.: PCT/US2018/018520
§ 371 (c)(1),
(2) Date: Aug. 9, 2019

(87) PCT Pub. No.: WO2018/152421
PCT Pub. Date: Aug. 23, 2018

(65) Prior Publication Data
US 2019/0365283 A1    Dec. 5, 2019

Related U.S. Application Data

(63) Continuation of application No. PCT/US2018/018405, filed on Feb. 15, 2018, and a
(Continued)

(51) Int. Cl.
*A61B 5/097* (2006.01)
*A61B 5/083* (2006.01)
(Continued)

(52) U.S. Cl.
CPC ............ *A61B 5/097* (2013.01); *A61B 5/0022* (2013.01); *A61B 5/0833* (2013.01);
(Continued)

(58) Field of Classification Search
CPC ...... A61B 5/097; A61B 5/0836; A61B 5/0022; A61B 5/0833; G01N 21/01; G01N 21/272;
(Continued)

(56) References Cited

U.S. PATENT DOCUMENTS

| | | |
|---|---|---|
| 3,368,872 A | 2/1968 | Natelson |
| 3,447,863 A | 6/1969 | Patterson |

(Continued)

FOREIGN PATENT DOCUMENTS

| | | |
|---|---|---|
| AU | 198813789 A | 9/1988 |
| AU | 619459 B | 1/1992 |

(Continued)

OTHER PUBLICATIONS

Van Vliet, Dillys et al., Prediction of asthma exacerbations in children by innovative exhaled inflammatory markers: Results of a longitudinal study, PLOS ONE, Mar. 23, 2015, vol. 10. No. 3, e0119434.
(Continued)

*Primary Examiner* — David Z Huang

(57) ABSTRACT

The present invention relates to provide, among other things, the methods, devices, and systems that can simply and quickly collecting and analyzing a tiny amount of vapor condensates (e.g. exhaled breath condensate (EBC)).

20 Claims, 9 Drawing Sheets

Related U.S. Application Data continuation of application No. PCT/US2018/018108, filed on Feb. 14, 2018, and a continuation of application No. PCT/US2018/018007, filed on Feb. 13, 2018, and a continuation of application No. PCT/US2018/017716, filed on Feb. 9, 2018, and a continuation of application No. PCT/US2018/017713, filed on Feb. 9, 2018, and a continuation of application No. PCT/US2018/017712, filed on Feb. 9, 2018, and a continuation of application No. PCT/US2018/017501, filed on Feb. 8, 2018, and a continuation of application No. PCT/US2018/017499, filed on Feb. 8, 2018, and a continuation of application No. PCT/US2018/017489, filed on Feb. 8, 2018, and a continuation of application No. PCT/US2018/017494, filed on Feb. 8, 2018, and a continuation of application No. PCT/US2018/017492, filed on Feb. 8, 2018, and a continuation of application No. PCT/US2018/017504, filed on Feb. 8, 2018, and a continuation of application No. PCT/US2018/017502, filed on Feb. 8, 2018, and a continuation of application No. PCT/US2018/017307, filed on Feb. 7, 2018.

(60) Provisional application No. 62/460,088, filed on Feb. 16, 2017, provisional application No. 62/459,920, filed on Feb. 16, 2017, provisional application No. 62/460,062, filed on Feb. 16, 2017, provisional application No. 62/460,083, filed on Feb. 16, 2017, provisional application No. 62/460,047, filed on Feb. 16, 2017, provisional application No. 62/460,069, filed on Feb. 16, 2017, provisional application No. 62/459,972, filed on Feb. 16, 2017, provisional application No. 62/460,076, filed on Feb. 16, 2017, provisional application No. 62/460,091, filed on Feb. 16, 2017, provisional application No. 62/460,075, filed on Feb. 16, 2017.

(51) Int. Cl.

| | |
|---|---|
| *A61B 5/00* | (2006.01) |
| *G01N 1/22* | (2006.01) |
| *G01N 1/30* | (2006.01) |
| *G01N 1/31* | (2006.01) |
| *G01N 33/543* | (2006.01) |
| *G01N 33/497* | (2006.01) |
| *G16H 10/40* | (2018.01) |
| *G16H 40/67* | (2018.01) |
| *B01L 3/00* | (2006.01) |
| *G01N 21/01* | (2006.01) |
| *G01N 21/27* | (2006.01) |
| *G01N 21/64* | (2006.01) |
| *G01N 21/78* | (2006.01) |
| *G06Q 40/08* | (2012.01) |
| *G01N 21/17* | (2006.01) |

(52) U.S. Cl.
CPC ............ *A61B 5/0836* (2013.01); *B01L 3/508* (2013.01); *G01N 1/22* (2013.01); *G01N 1/30* (2013.01); *G01N 1/31* (2013.01); *G01N 21/01* (2013.01); *G01N 21/272* (2013.01); *G01N 21/645* (2013.01); *G01N 21/78* (2013.01); *G01N 33/497* (2013.01); *G01N 33/54306* (2013.01); *G01N 33/54386* (2013.01); *G16H 10/40* (2018.01); *G16H 40/67* (2018.01); *B01L 2300/0654* (2013.01); *B01L 2300/0816* (2013.01); *B01L 2300/0851* (2013.01); *B01L 2300/123* (2013.01); *B01L 2300/168* (2013.01); *B01L 2400/0406* (2013.01); *G01N 21/17* (2013.01); *G01N 2001/2244* (2013.01); *G01N 2001/302* (2013.01); *G01N 2021/1776* (2013.01); *G01N 2033/4975* (2013.01); *G06Q 40/08* (2013.01)

(58) Field of Classification Search
CPC ........... G01N 21/78; G01N 1/22; G01N 1/31; G01N 33/54386; G01N 33/54306; G01N 33/497; G01N 2001/2244; G01N 2001/302; G01N 2033/4975; G01N 2021/1776; G16H 10/40
See application file for complete search history.

(56) References Cited

U.S. PATENT DOCUMENTS

| | | |
|---|---|---|
| 3,895,661 A | 7/1975 | Praglin et al. |
| 3,925,166 A | 12/1975 | Blume |
| 3,992,158 A | 11/1976 | Przybylowicz et al. |
| 4,022,521 A | 5/1977 | Hall et al. |
| 4,066,412 A | 1/1978 | Johnson et al. |
| 4,088,448 A | 5/1978 | Lilja et al. |
| 4,171,866 A | 10/1979 | Tolles |
| 4,233,029 A | 11/1980 | Columbus |
| 4,255,384 A | 3/1981 | Kitajima et al. |
| 4,258,001 A | 3/1981 | Pierce et al. |
| 4,329,054 A | 5/1982 | Bachalo |
| 4,402,614 A | 9/1983 | Porath |
| 4,427,294 A | 1/1984 | Pietro |
| 4,430,436 A | 2/1984 | Koyama et al. |
| 4,596,695 A | 6/1986 | Cottingham |
| 4,745,075 A | 5/1988 | Hadfield et al. |
| 4,806,311 A | 2/1989 | Greenquist |
| 4,883,642 A | 11/1989 | Bisconte |
| 4,906,439 A | 3/1990 | Grenner |
| 4,911,782 A | 3/1990 | Brown |
| 4,950,455 A | 8/1990 | Smith |
| 5,002,736 A | 3/1991 | Babbitt et al. |
| 5,039,487 A | 8/1991 | Smith |
| 5,096,836 A | 3/1992 | Macho et al. |
| 5,122,284 A | 6/1992 | Braynin et al. |
| 5,132,097 A | 7/1992 | Van Deusen et al. |
| 5,169,601 A | 12/1992 | Ohta et al. |
| 5,188,968 A | 2/1993 | Kano et al. |
| 5,223,219 A | 6/1993 | Subramanian et al. |
| 5,281,540 A | 1/1994 | Merkh et al. |
| 5,306,467 A | 4/1994 | Douglas-Hamilton et al. |
| 5,321,975 A | 6/1994 | Wardlaw |
| 5,362,648 A | 11/1994 | Koreyasu et al. |
| 5,413,732 A | 5/1995 | Buhl et al. |
| 5,427,959 A | 6/1995 | Nishimura et al. |
| 5,431,880 A | 7/1995 | Kramer |
| 5,591,403 A | 1/1997 | Gavin et al. |
| 5,623,415 A | 4/1997 | O'Bryan et al. |
| 5,753,456 A | 5/1998 | Naqui et al. |
| 5,768,407 A | 6/1998 | Shen et al. |
| 5,858,648 A | 1/1999 | Steel et al. |
| 5,879,628 A | 3/1999 | Ridgeway et al. |
| 5,888,834 A | 3/1999 | Ishikawa et al. |
| 5,939,326 A | 8/1999 | Chupp et al. |
| 5,948,686 A | 9/1999 | Wardlaw |
| 6,004,821 A | 12/1999 | Levine et al. |
| 6,016,367 A | 1/2000 | Benedetti et al. |
| 6,017,767 A | 1/2000 | Chandler |
| 6,022,734 A | 2/2000 | Wardlaw |
| 6,106,778 A | 8/2000 | Oku et al. |
| 6,180,314 B1 | 1/2001 | Berndt |
| 6,235,536 B1 | 5/2001 | Wardlaw |
| 6,284,384 B1 | 9/2001 | Wilson et al. |
| 6,350,613 B1 | 2/2002 | Wardlaw et al. |
| 6,358,475 B1 | 3/2002 | Berndt |
| 6,429,027 B1 | 8/2002 | Chee et al. |
| 6,503,760 B2 | 1/2003 | Malmqvist et al. |
| 6,551,554 B1 | 4/2003 | Vermeiden et al. |
| 6,623,701 B1 | 9/2003 | Eichele et al. |

(56) References Cited

U.S. PATENT DOCUMENTS

| | | |
|---|---|---|
| 6,632,652 B1 | 10/2003 | Austin et al. |
| 6,714,287 B2 | 3/2004 | Berndt |
| 6,723,290 B1 | 4/2004 | Wardlaw |
| 6,844,201 B2 | 1/2005 | Malmqvist et al. |
| 6,866,823 B2 | 3/2005 | Wardlaw |
| 6,869,570 B2 | 3/2005 | Wardlaw |
| 6,893,850 B2 | 5/2005 | Ostuni et al. |
| 6,906,700 B1 | 6/2005 | Armstrong et al. |
| 6,921,514 B1 | 7/2005 | Vetter et al. |
| 6,929,953 B1 | 8/2005 | Wardlaw |
| 6,939,032 B2 | 9/2005 | Cosby et al. |
| 7,101,341 B2 | 9/2006 | Tsukashima et al. |
| 7,179,423 B2 | 2/2007 | Bohm et al. |
| 7,282,367 B2 | 10/2007 | Kawamura |
| 7,393,658 B2 | 7/2008 | Carbonell et al. |
| 7,410,617 B2 | 8/2008 | Sakamoto |
| 7,410,807 B2 | 8/2008 | D'Aurora |
| 7,468,160 B2 | 12/2008 | Thompson et al. |
| 7,510,841 B2 | 3/2009 | Stuelpnagel et al. |
| 7,510,848 B2 | 3/2009 | Hammond et al. |
| 7,547,424 B2 | 6/2009 | Haab et al. |
| 7,731,901 B2 | 6/2010 | Wardlaw |
| 7,738,094 B2 | 6/2010 | Goldberg |
| 7,850,916 B2 | 12/2010 | Wardlaw |
| 7,862,773 B2 | 1/2011 | Ibrahim |
| 7,863,411 B2 | 1/2011 | Hammond et al. |
| 7,897,376 B2 | 3/2011 | Porter et al. |
| 7,901,897 B2 | 3/2011 | Stuelpnagel et al. |
| 7,903,241 B2 | 3/2011 | Wardlaw et al. |
| 7,929,121 B2 | 4/2011 | Wardlaw et al. |
| 7,929,122 B2 | 4/2011 | Wardlaw et al. |
| 7,943,093 B2 | 5/2011 | Adrien et al. |
| 7,951,599 B2 | 5/2011 | Levine et al. |
| 7,995,194 B2 | 8/2011 | Wardlaw et al. |
| 8,045,165 B2 | 10/2011 | Wardlaw et al. |
| 8,058,073 B2 | 11/2011 | Chiapperi et al. |
| 8,077,296 B2 | 12/2011 | Wardlaw et al. |
| 8,081,303 B2 | 12/2011 | Levine et al. |
| 8,133,738 B2 | 3/2012 | Levine et al. |
| 8,158,434 B2 | 4/2012 | Wardlaw |
| 8,221,985 B2 | 7/2012 | Wardlaw et al. |
| 8,241,572 B2 | 8/2012 | Wardlaw |
| 8,269,954 B2 | 9/2012 | Levine et al. |
| 8,287,820 B2 | 10/2012 | Williams et al. |
| 8,310,658 B2 | 11/2012 | Wardlaw et al. |
| 8,310,659 B2 | 11/2012 | Wardlaw et al. |
| 8,319,954 B2 | 11/2012 | Wardlaw et al. |
| 8,326,008 B2 | 12/2012 | Lalpuria et al. |
| 8,338,579 B2 | 12/2012 | Adams et al. |
| 8,361,799 B2 | 1/2013 | Levine et al. |
| 8,367,012 B2 | 2/2013 | Wardlaw |
| 8,462,332 B2 | 6/2013 | Pugia et al. |
| 8,467,063 B2 | 6/2013 | Wardlaw et al. |
| 8,472,693 B2 | 6/2013 | Davis et al. |
| 8,481,282 B2 | 7/2013 | Levine et al. |
| 8,502,963 B2 | 8/2013 | Levine et al. |
| 8,513,032 B2 | 8/2013 | Jablonski et al. |
| 8,569,076 B2 | 10/2013 | Wardlaw et al. |
| 8,594,768 B2 | 11/2013 | Phillips et al. |
| 8,604,161 B2 | 12/2013 | Hammond et al. |
| 8,628,952 B2 | 1/2014 | Stuelpnagel et al. |
| 8,633,013 B2 | 1/2014 | Kaiser et al. |
| 8,638,427 B2 | 1/2014 | Wardlaw et al. |
| 8,717,673 B2 | 5/2014 | Selvin et al. |
| 8,741,630 B2 | 6/2014 | Dickinson et al. |
| 8,750,966 B2 | 6/2014 | Phillips et al. |
| 8,778,687 B2 | 7/2014 | Levine et al. |
| 8,781,203 B2 | 7/2014 | Davis et al. |
| 8,796,186 B2 | 8/2014 | Shirazi |
| 8,797,527 B2 | 8/2014 | Hukari et al. |
| 8,835,186 B2 | 9/2014 | Jablonski et al. |
| 8,837,803 B2 | 9/2014 | Wang et al. |
| 8,842,264 B2 | 9/2014 | Wardlaw et al. |
| 8,885,154 B2 | 11/2014 | Wardlaw et al. |
| 8,911,815 B2 | 12/2014 | Kram et al. |
| 8,974,732 B2 | 3/2015 | Lalpuria et al. |
| 8,994,930 B2 | 3/2015 | Levine et al. |
| 9,023,641 B2 | 5/2015 | Rodriguez et al. |
| 9,044,268 B2 | 6/2015 | Phillips et al. |
| 9,046,473 B2 | 6/2015 | Levine et al. |
| 9,084,995 B2 | 7/2015 | Wardlaw |
| 9,086,408 B2 | 7/2015 | Egan et al. |
| 9,097,640 B2 | 8/2015 | Goldberg et al. |
| 9,199,233 B2 | 12/2015 | Wardlaw |
| 9,274,094 B2 | 3/2016 | Wardlaw et al. |
| 9,291,617 B2 | 3/2016 | Levine et al. |
| 9,322,835 B2 | 4/2016 | Wardlaw |
| 9,347,962 B2 | 5/2016 | Salsman |
| 9,354,159 B2 | 5/2016 | Vaartstra |
| 9,395,365 B2 | 7/2016 | Levine et al. |
| 9,469,871 B2 | 10/2016 | Bearinger et al. |
| 9,523,670 B2 | 12/2016 | Mueller et al. |
| 9,696,252 B2 | 7/2017 | Wardlaw |
| 2001/0055882 A1 | 12/2001 | Ostuni |
| 2003/0068614 A1 | 4/2003 | Cima et al. |
| 2003/0107946 A1 | 6/2003 | Cosby et al. |
| 2003/0109059 A1 | 6/2003 | Adrien et al. |
| 2004/0131345 A1 | 7/2004 | Kylberg et al. |
| 2004/0156755 A1 | 8/2004 | Levine |
| 2004/0214310 A1 | 10/2004 | Parker et al. |
| 2004/0259162 A1 | 12/2004 | Kappel et al. |
| 2005/0026161 A1 | 2/2005 | Jablonski et al. |
| 2005/0032138 A1 | 2/2005 | Lathrop et al. |
| 2005/0158880 A1 | 7/2005 | Ostuni et al. |
| 2005/0254995 A1 | 11/2005 | Sostek et al. |
| 2006/0015157 A1 | 1/2006 | Leong |
| 2006/0051253 A1 | 3/2006 | Gousepohl |
| 2006/0062440 A1 | 3/2006 | Hollars et al. |
| 2006/0062695 A1 | 3/2006 | Haab et al. |
| 2006/0090658 A1 | 5/2006 | Phillips |
| 2006/0160134 A1 | 7/2006 | Melker et al. |
| 2007/0087442 A1 | 4/2007 | Wardlaw |
| 2007/0243117 A1 | 10/2007 | Wardlaw |
| 2008/0028962 A1 | 2/2008 | Phillips et al. |
| 2008/0214947 A1 | 9/2008 | Hunt et al. |
| 2008/0274564 A1 | 11/2008 | D'Aurora |
| 2008/0286152 A1 | 11/2008 | Schmidt et al. |
| 2009/0211344 A1 | 8/2009 | Wang |
| 2009/0227472 A1 | 9/2009 | Stuelpnagel et al. |
| 2009/0233329 A1 | 9/2009 | Rodriguez et al. |
| 2009/0246781 A1 | 10/2009 | Klem et al. |
| 2009/0258371 A1 | 10/2009 | Wardlaw et al. |
| 2009/0298716 A1 | 12/2009 | Stuelpnagel et al. |
| 2010/0081583 A1 | 4/2010 | Shirazi |
| 2010/0085067 A1 | 4/2010 | Gabriel et al. |
| 2010/0151593 A1 | 6/2010 | D'Aurora |
| 2010/0216248 A1 | 8/2010 | Wardlaw |
| 2010/0255605 A1 | 10/2010 | Wardlaw |
| 2010/0272345 A1 | 10/2010 | Wardlaw |
| 2010/0273244 A1 | 10/2010 | Wardlaw |
| 2010/0291562 A1 | 11/2010 | Adler |
| 2011/0009297 A1 | 1/2011 | Jones et al. |
| 2011/0206557 A1 | 8/2011 | Phan et al. |
| 2011/0294198 A1 | 12/2011 | Wardlaw |
| 2012/0034647 A1 | 2/2012 | Herzog et al. |
| 2012/0107799 A1 | 5/2012 | Daum |
| 2012/0108787 A1 | 5/2012 | Lue |
| 2012/0157332 A1 | 6/2012 | Kumar et al. |
| 2012/0300293 A1 | 11/2012 | Selvin et al. |
| 2013/0065788 A1 | 3/2013 | Glezer et al. |
| 2013/0102018 A1* | 4/2013 | Schentag ........... A61B 5/14507 435/25 |
| 2013/0157288 A1 | 6/2013 | Kilfeather et al. |
| 2013/0209332 A1 | 8/2013 | Wardlaw |
| 2013/0265054 A1 | 10/2013 | Lowery et al. |
| 2013/0309679 A1 | 11/2013 | Ismagilov et al. |
| 2014/0206976 A1* | 7/2014 | Thompson ............. G06F 19/00 600/391 |
| 2014/0315242 A1 | 10/2014 | Rodriguez et al. |
| 2014/0368631 A1 | 12/2014 | Wardlaw et al. |
| 2015/0036131 A1 | 2/2015 | Salsman |
| 2015/0253321 A1 | 9/2015 | Chou et al. |
| 2015/0317506 A1 | 11/2015 | Xie et al. |
| 2015/0323519 A1 | 11/2015 | Wardlaw |

(56) References Cited

U.S. PATENT DOCUMENTS

| | | | |
|---|---|---|---|
| 2016/0025637 A1* | 1/2016 | Halverson | G01N 21/55 506/12 |
| 2016/0033496 A1 | 2/2016 | Chou et al. | |
| 2016/0192861 A1* | 7/2016 | Gedeon | A61B 5/0816 600/532 |
| 2016/0245797 A1 | 8/2016 | Ahmad et al. | |
| 2016/0266091 A1 | 9/2016 | Levine et al. | |
| 2017/0021356 A1 | 1/2017 | Dority et al. | |
| 2017/0038401 A1 | 2/2017 | Holmes et al. | |
| 2017/0045504 A1 | 2/2017 | Bloom | |
| 2017/0219573 A1* | 8/2017 | Needham | G01N 33/56916 |

FOREIGN PATENT DOCUMENTS

| | | |
|---|---|---|
| CN | 1299466 | 6/2001 |
| CN | 1302229 | 7/2001 |
| CN | 1166950 | 9/2004 |
| CN | 1188217 | 2/2005 |
| CN | 102027369 | 4/2011 |
| EP | 261667 A2 | 3/1988 |
| EP | 291153 A1 | 11/1988 |
| EP | 261667 A3 | 5/1989 |
| EP | 291153 B1 | 6/1992 |
| EP | 261667 B1 | 2/1993 |
| EP | 0961110 | 12/1999 |
| EP | 1949310 A2 | 7/2008 |
| EP | 2290100 | 3/2011 |
| EP | 1949310 A4 | 11/2011 |
| EP | 2439515 | 4/2012 |
| EP | 2554987 | 2/2013 |
| EP | 3026433 | 6/2016 |
| EP | 1949310 B1 | 2/2019 |
| WO | 1991020009 | 12/1991 |
| WO | 1999044743 | 9/1999 |
| WO | 1999045385 | 9/1999 |
| WO | 2003062920 | 7/2003 |
| WO | 2005114145 | 12/2005 |
| WO | 2005100539 | 1/2006 |
| WO | 2007112332 | 10/2007 |
| WO | 2009117652 | 9/2009 |
| WO | 2009117664 | 9/2009 |
| WO | 2009117678 | 9/2009 |
| WO | 2009117682 | 9/2009 |
| WO | 2009124186 | 10/2009 |
| WO | 2009124190 | 10/2009 |
| WO | 2009126800 | 10/2009 |
| WO | 2010115026 | 10/2010 |
| WO | 2014055559 | 4/2014 |
| WO | 2014089468 | 6/2014 |
| WO | 2014183049 | 11/2014 |
| WO | 2014205576 | 12/2014 |
| WO | 2017048871 | 3/2017 |

OTHER PUBLICATIONS

Written Opinion for PCT/US2018/017713 established by ISA/KR, dated Jun. 20, 2018.

* cited by examiner

Fig. 1. Exemplary device and methods of collecting exhaled breath condensate (EBC) using a SiEBC (Single-drop EBC Collector/Analyzer), that comprises a pair of movable plates without using spacers.

1. Exhaling breath onto collection plate

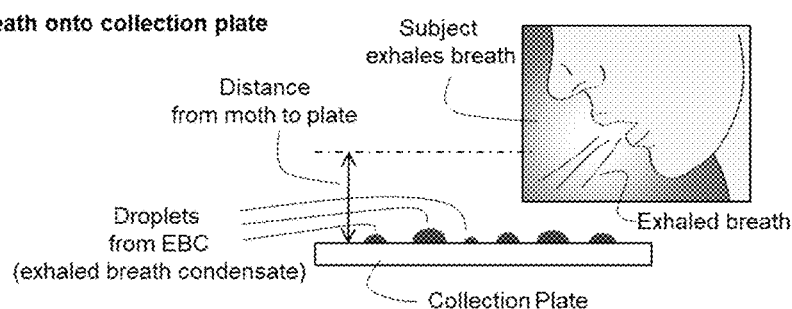

2. Placing cover plate over collection plate and pressing them together

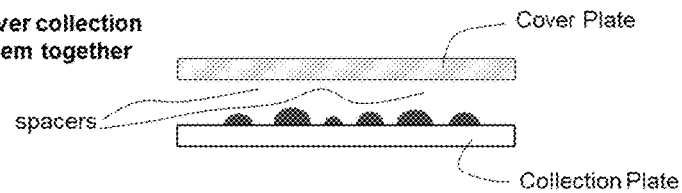

3. Pressing plates into a "Closed-Configuration", where the initial droplets are pressed into a thin layer EBC of a thickness that is regulated by the plates and spacers (not shown).

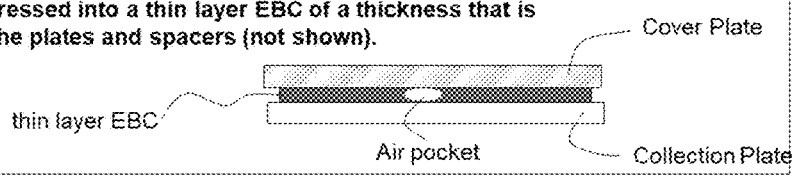

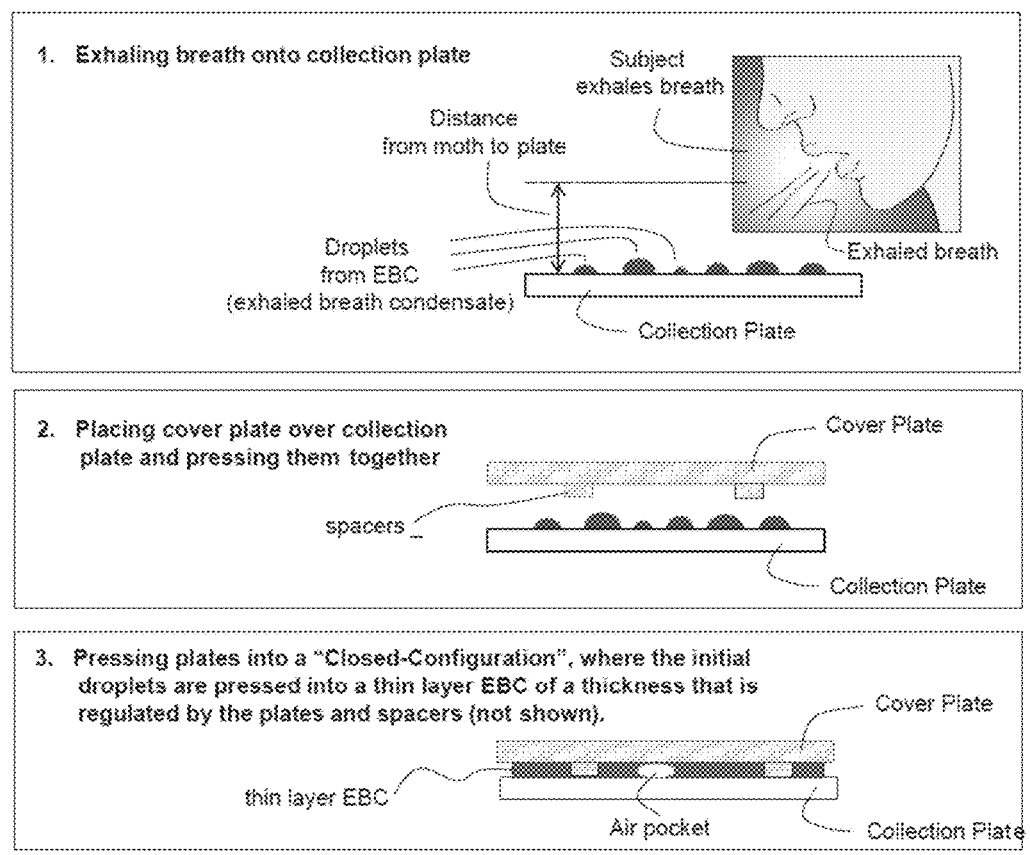
Fig. 2. Exemplary device and methods of collecting exhaled breath condensate (EBC) using a SiEBC (Single-drop EBC Collector/Analyzer)

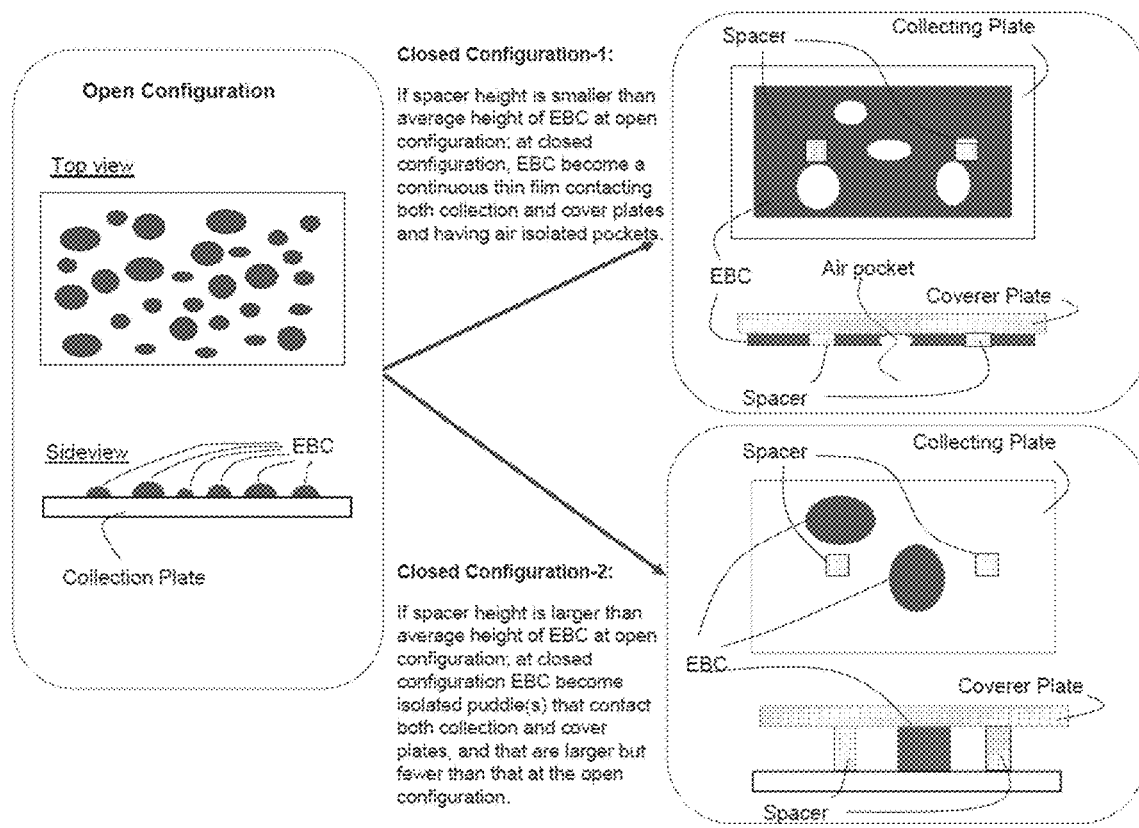
Fig. 3 Different formations of EBC at closed configuration of SiEBCA depends on spacer height Fig. 4. An illustration of a SiEBC (Single-drop EBC Collector/Analyzer) embodiment.
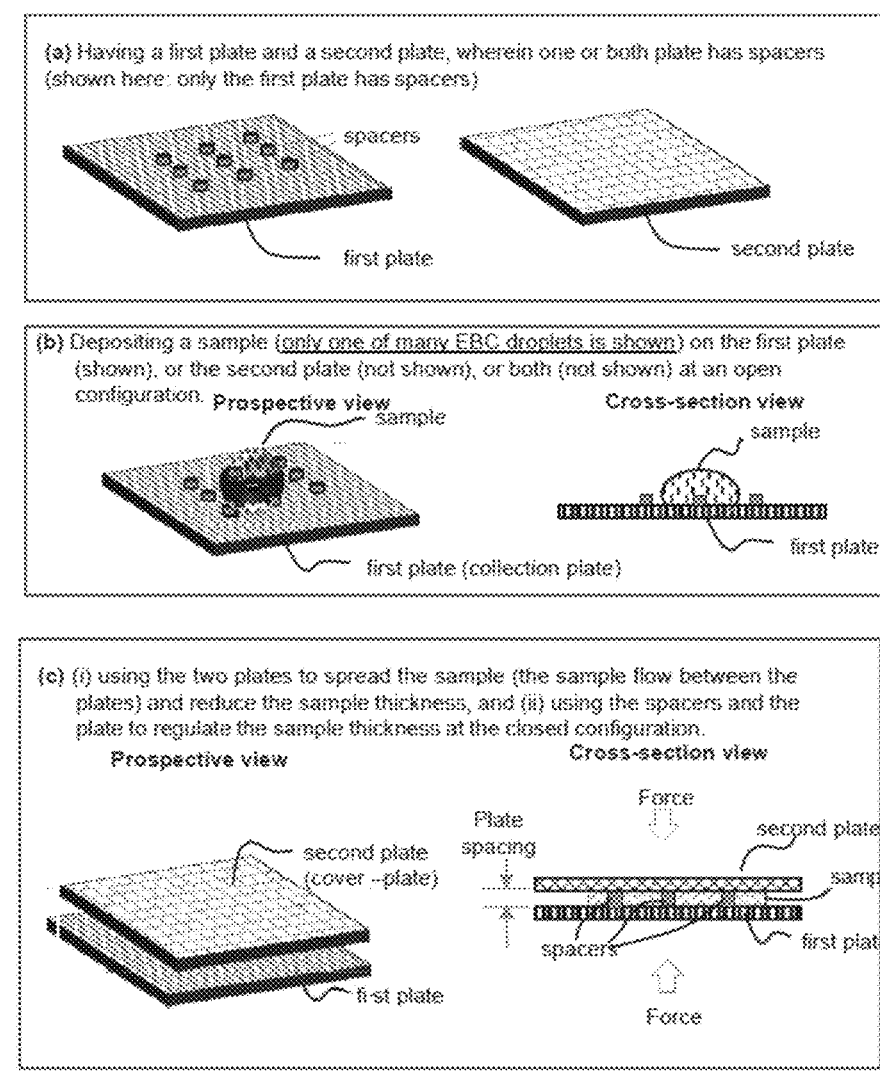

(A) Liquid thickness measurements:
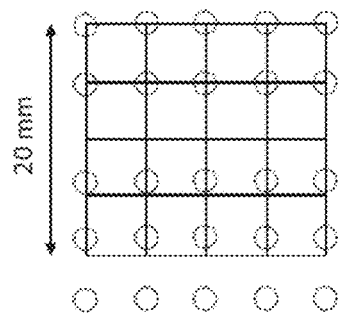
(B) Liquid area measurements:
From direct photo of QMAX after closing:
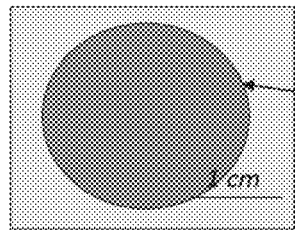
Determine overall sample area.
From microscopy of QMAX after closing:
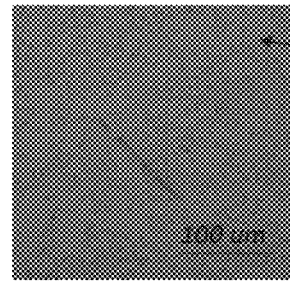
Recognize and determine bubble area.
Fig. 6

ASSAY FOR VAPOR CONDENSATES

CROSS-REFERENCE TO RELATED APPLICATIONS

This application is a § 371 national stage application of International Application PCT/US2018/018520 filed on Feb. 16, 2018, which claims the benefit of priority to U.S. Provisional Application ("USPA" hereinafter) No. 62/460,088, filed on Feb. 16, 2017, USPA No. 62/460,091, filed on Feb. 16, 2017, USPA No. 62/460,083, filed on Feb. 16, 2017, USPA No. 62/460,076, filed on Feb. 16, 2017, USPA No. 62/460,075, filed on Feb. 16, 2017, USPA No. 62/460,069, filed on Feb. 16, 2017, USPA No. 62/460,062, filed on Feb. 16, 2017, USPA No. 62/460,047, filed on Feb. 16, 2017, USPA No. 62/459,972, filed on Feb. 16, 2017, USPA No. 62/459,920, filed on Feb. 16, 2017, PCT Application No. PCT/US18/18405, filed on Feb. 15, 2018, PCT Application No. PCT/US18/18108, filed on Feb. 14, 2018, PCT Application No. PCT/US18/18007, filed on Feb. 13, 2018, PCT Application No. PCT/US18/17716, filed on Feb. 9, 2018, PCT Application No. PCT/US18/17713, filed on Feb. 9, 2018, PCT Application No. PCT/US18/17712, filed on Feb. 9, 2018, PCT Application No. PCT/US18/17504, filed on Feb. 8, 2018, PCT Application No. PCT/US18/17501, filed on Feb. 8, 2018, PCT Application No. PCT/US18/17499, filed on Feb. 8, 2018, PCT Application No. PCT/US18/17489, filed on Feb. 8, 2018, PCT Application No. PCT/US18/17492, filed on Feb. 8, 2018, PCT Application No. PCT/US18/17494, filed on Feb. 8, 2018, PCT Application No. PCT/US18/17502, filed on Feb. 8, 2018, and PCT Application No. PCT/US18/17307, filed on Feb. 7, 2018, the contents of which are relied upon and incorporated herein by reference in their entirety. The entire disclosure of any publication or patent document mentioned herein is entirely incorporated by reference.

FIELD

The present invention is related to the field of bio/chemical sampling, sensing, assays and applications.

BACKGROUND

In bio/chemical vapor condensate sample analysis, particularly exhaled breath condensate (EBC), there is a need for methods and devices that can simplify the sample collection and measurement processes, that can accelerate the process (e.g. binding, mixing reagents, etc.) and quantify the parameters (e.g. analyte concentration, the sample volume, etc.), that can handle samples with small volume, that allow an entire assay performed in less than a minute, that allow an assay performed by a smartphone (e.g. mobile phone), that allow non-professional to perform an assay her/himself, and that allow a test result to be communicated locally, remotely, or wirelessly to different relevant parties.

The present invention relates to provide, among other things, the methods, devices, and systems that can address these needs.

SUMMARY OF INVENTION

The following brief summary is not intended to include all features and aspects of the present invention.

The present invention is related to provide, among other things, the device, apparatus, systems, and methods for: (i) rapidly and simply collecting a tiny amount (a volume as small as 10 fL (femto-Liter) in a single drop) of a vapor condensate sample (e.g. the exhaled breath condensate (EBC) from a subject), (ii) preventing or significantly reducing an evaporation of the collected vapor condensate sample, (iii) analyzing the sample, analyzing the sample by mobile-phone, (iv) and performing such collection and analysis by a person without any professionals; (v) the devices can get the sample thickness information either using spacers or without a spacers.

Since the exhaled breath condensate (EBC) and other vapor condensate share many common properties, the disclosure uses EBC as a representative to illustrate certain embodiments of the present invention, but such presentation should not be construed as any limitations of the present invention.

BRIEF DESCRIPTION OF THE DRAWINGS

The skilled artisan will understand that the drawings, described below, are for illustration purposes only. The drawings are not intended to limit the scope of the present teachings in any way. The drawings may not be in scale. In the figures that present experimental data points, the lines that connect the data points are for guiding a viewing of the data only and have no other means.

FIG. 1. An illustration of certain aspects of an exemplary device and methods of collecting exhaled breath condensate (EBC) using a SiEBCA (Single-drop EBC Collector/Analyzer), that comprises a pair of movable plates without using spacers.

FIG. 2. An illustration of certain aspects of an exemplary device and methods of collecting exhaled breath condensate (EBC) using a SiEBCA (Single-drop EBC Collector/Analyzer).

FIG. 3. An illustration of different formations of EBC at closed configuration of SiEBCA depends on spacer height. In closed configuration-1: If spacer height is smaller than average height of EBC at open configuration; at closed configuration, EBC become a continuous thin film contacting both collection and cover plates and may have air isolated pockets. In the closed configuration-2: If spacer height is larger than average height of EBC at open configuration; at closed configuration EBC become isolated puddle(s) that contact both collection and cover plates, and that are larger but fewer than that at the open configuration.

FIG. 4. An illustration of an embodiment of the devices and the methods of a SiEBCA (Single-drop EBC Collector/Analyzer).

FIG. 6 schematically illustrates the optical measurement and imaging taken for the measurement of the EBC sample thickness and lateral area, respectively.

DETAILED DESCRIPTION OF EXEMPLARY EMBODIMENTS

Figure 5A:
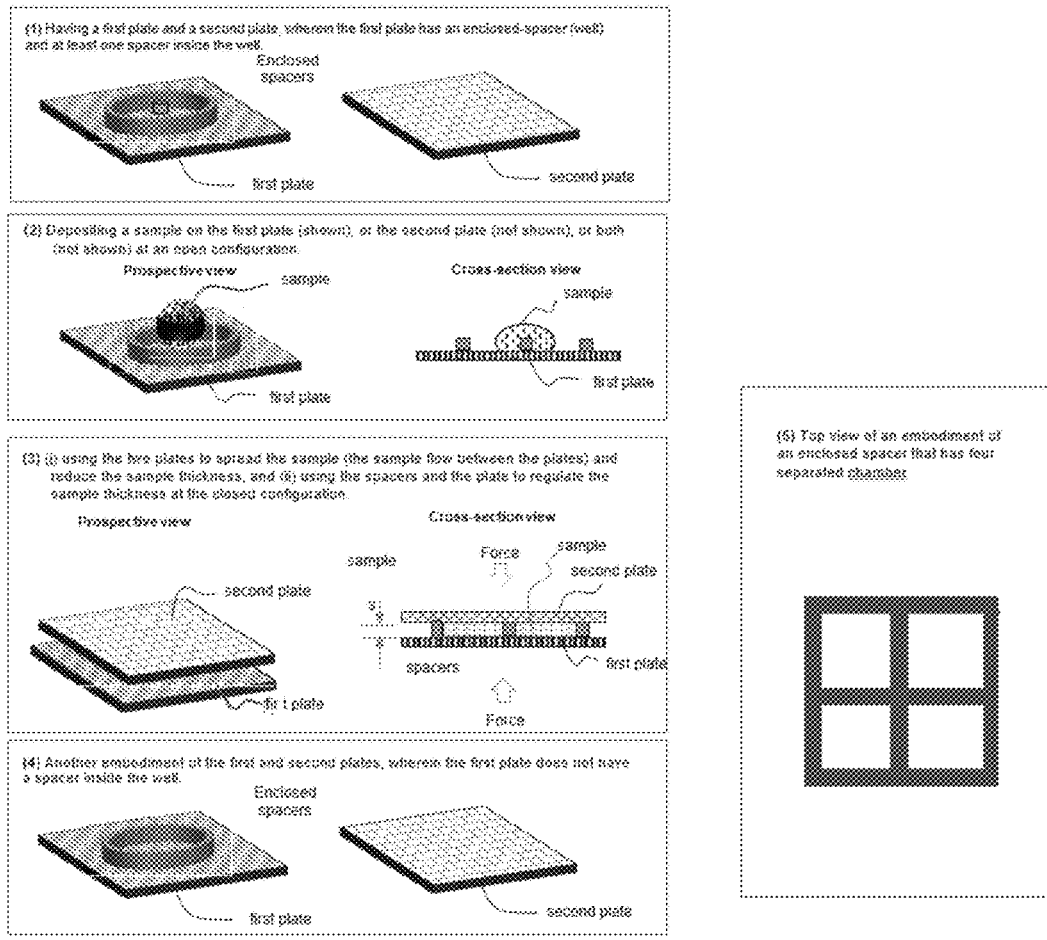
FIG. 5a An illustration of a SiEBCA with both "open spacer" and "enclosed spacer", where the open spacer is a post (pillar) while the enclosed spacer is a ring spacer (4) and a four-chamber grid spacer (5).

The following detailed description illustrates some embodiments of the invention by way of example and not by way of limitation. If any, the section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

Definitions

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The terms "exhaled breath condensate (EBC)" and "vapor condensate (VC)" are, unless specifically stated, interchangeable.

The term "SiEBCA" and "SiEBC" are interchangeable.

The terms "polynucleotide", "nucleotide", "nucleotide sequence", "nucleic acid", "nucleic acid molecule", "nucleic acid sequence" and "oligonucleotide" are used interchangeably, and can also include plurals of each respectively depending on the context in which the terms are utilized. The term "capture agent" as used herein, refers to a binding member, e.g. nucleic acid molecule, polypeptide molecule, or any other molecule or compound, that can specifically bind to its binding partner, e.g., a second nucleic acid molecule containing nucleotide sequences complementary to a first nucleic acid molecule, an antibody that specifically recognizes an antigen, an antigen specifically recognized by an antibody, a nucleic acid aptamer that can specifically bind to a target molecule, etc.

The term "a secondary capture agent" which can also be referred to as a "detection agent" refers a group of biomolecules or chemical compounds that have highly specific affinity to the antigen. The secondary capture agent can be strongly linked to an optical detectable label, e.g., enzyme, fluorescence label, or can itself be detected by another detection agent that is linked to an optical detectable label through bioconjugation (Hermanson, "Bioconjugate Techniques" Academic Press, 2nd Ed., 2008).

The term "capture agent-reactive group" refers to a moiety of chemical function in a molecule that is reactive with capture agents, i.e., can react with a moiety (e.g., a hydroxyl, sulfhydryl, carboxyl or amine group) in a capture agent to produce a stable strong, e.g., covalent bond.

The terms "specific binding" and "selective binding" refer to the ability of a capture agent to preferentially bind to a particular target analyte that is present in a heterogeneous mixture of different target analytes. A specific or selective binding interaction will discriminate between desirable (e.g., active) and undesirable (e.g., inactive) target analytes in a sample, typically more than about 10 to 100-fold or more (e.g., more than about 1000- or 10,000-fold).

The term "analyte" refers to a molecule (e.g., a protein, peptides, DNA, RNA, nucleic acid, or other molecule), cells, tissues, viruses, and nanoparticles with different shapes.

The term "assaying" refers to testing a sample to detect the presence and/or abundance of an analyte.

As used herein, the terms "determining," "measuring," and "assessing," and "assaying" are used interchangeably and include both quantitative and qualitative determinations.

As used herein, the term "light-emitting label" refers to a label that can emit light when under an external excitation. This can be luminescence. Fluorescent labels (which include dye molecules or quantum dots), and luminescent labels (e.g., electro- or chemi-luminescent labels) are types of light-emitting label. The external excitation is light (photons) for fluorescence, electrical current for electroluminescence and chemical reaction for chemi-luminescence. An external excitation can be a combination of the above.

The phrase "labeled analyte" refers to an analyte that is detectably labeled with a light emitting label such that the analyte can be detected by assessing the presence of the label. A labeled analyte may be labeled directly (i.e., the analyte itself may be directly conjugated to a label, e.g., via a strong bond, e.g., a covalent or non-covalent bond), or a labeled analyte may be labeled indirectly (i.e., the analyte is bound by a secondary capture agent that is directly labeled).

The terms "hybridizing" and "binding", with respect to nucleic acids, are used interchangeably.

The term "capture agent/analyte complex" is a complex that results from the specific binding of a capture agent with an analyte. A capture agent and an analyte for the capture agent will usually specifically bind to each other under "specific binding conditions" or "conditions suitable for specific binding", where such conditions are those conditions (in terms of salt concentration, pH, detergent, protein concentration, temperature, etc.) which allow for binding to occur between capture agents and analytes to bind in solution. Such conditions, particularly with respect to antibodies and their antigens and nucleic acid hybridization are well known in the art (see, e.g., Harlow and Lane (Antibodies: A Laboratory Manual Cold Spring Harbor Laboratory, Cold Spring Harbor, N.Y. (1989) and Ausubel, et al, Short Protocols in Molecular Biology, 5th ed., Wiley & Sons, 2002).

A subject may be any human or non-human animal. A subject may be a person performing the instant method, a patient, a customer in a testing center, etc.

As used herein, a "diagnostic sample" refers to any biological sample that is a bodily byproduct, such as bodily fluids, that has been derived from a subject. The diagnostic sample may be obtained directly from the subject in the form of liquid, or may be derived from the subject by first placing the bodily byproduct in a solution, such as a buffer. Exemplary diagnostic samples include, but are not limited to, saliva, serum, blood, sputum, urine, sweat, lacrima, semen, feces, breath, biopsies, mucus, etc.

As used herein, an "environmental sample" refers to any sample that is obtained from the environment. An environmental sample may include liquid samples from a river, lake, pond, ocean, glaciers, icebergs, rain, snow, sewage, reservoirs, tap water, drinking water, etc.; solid samples from soil, compost, sand, rocks, concrete, wood, brick, sewage, etc.; and gaseous samples from the air, underwater heat vents, industrial exhaust, vehicular exhaust, etc. Typically, samples that are not in liquid form are converted to liquid form before analyzing the sample with the present method.

As used herein, a "foodstuff sample" refers to any sample that is suitable for animal consumption, e.g., human consumption. A foodstuff sample may include raw ingredients, cooked food, plant and animal sources of food, preprocessed food as well as partially or fully processed food, etc. Typically, samples that are not in liquid form are converted to liquid form before analyzing the sample with the present method.

The term "diagnostic," as used herein, refers to the use of a method or an analyte for identifying, predicting the outcome of and/or predicting treatment response of a disease or condition of interest. A diagnosis may include predicting the likelihood of or a predisposition to having a disease or condition, estimating the severity of a disease or condition, determining the risk of progression in a disease or condition, assessing the clinical response to a treatment, and/or predicting the response to treatment.

A "biomarker," as used herein, is any molecule or compound that is found in a sample of interest and that is known to be diagnostic of or associated with the presence of or a predisposition to a disease or condition of interest in the subject from which the sample is derived. Biomarkers include, but are not limited to, polypeptides or a complex thereof (e.g., antigen, antibody), nucleic acids (e.g., DNA, miRNA, mRNA), drug metabolites, lipids, carbohydrates, hormones, vitamins, etc., that are known to be associated with a disease or condition of interest.

A "condition" as used herein with respect to diagnosing a health condition, refers to a physiological state of mind or body that is distinguishable from other physiological states. A health condition may not be diagnosed as a disease in some cases. Exemplary health conditions of interest include, but are not limited to, nutritional health; aging; exposure to environmental toxins, pesticides, herbicides, synthetic hormone analogs; pregnancy; menopause; andropause; sleep; stress; prediabetes; exercise; fatigue; chemical balance; etc.

The term "entity" refers to, but not limited to proteins, peptides, DNA, RNA, nucleic acid, molecules (small or large), cells, tissues, viruses, nanoparticles with different shapes, that would bind to a "binding site". The entity includes the capture agent, detection agent, and blocking agent.

The "entity" includes the "analyte", and the two terms are used interchangeably.

The term "binding site" refers to a location on a solid surface that can immobilize an entity in a sample.

The term "entity partners" refers to, but not limited to proteins, peptides, DNA, RNA, nucleic acid, molecules (small or large), cells, tissues, viruses, nanoparticles with different shapes, that are on a "binding site" and would bind to the entity. The entity, include, but not limited to, capture agents, detection agents, secondary detection agents, or "capture agent/analyte complex".

The term "smart phone" or "mobile phone", which are used interchangeably, refers to the type of phones that has a camera and communication hardware and software that can take an image using the camera, manipulate the image taken by the camera, and communicate data to a remote place. In some embodiments, the Smart Phone has a flash light.

The term "average linear dimension" of an area is defined as a length that equals to the area times 4 then divided by the perimeter of the area. For example, the area is a rectangle, that has width w, and length L, then the average of the linear dimension of the rectangle is $4*W*L/(2*(L+W))$ (where "*" means multiply and "/" means divide). By this definition, the average line dimension is, respectively, W for a square of a width W, and d for a circle with a diameter d. The area includes, but not limited to, the area of a binding site or a storage site.

The term "period" of periodic structure array refers to the distance from the center of a structure to the center of the nearest neighboring identical structure.

The term "storage site" refers to a site of an area on a plate, wherein the site contains reagents to be added into a sample, and the reagents are capable of being dissolving into the sample that is in contract with the reagents and diffusing in the sample.

The term "relevant" means that it is relevant to detection of analytes, quantification and/or control of analyte or entity in a sample or on a plate, or quantification or control of reagent to be added to a sample or a plate.

The term "hydrophilic", "wetting", or "wet" of a surface means that the contact angle of a sample on the surface is less than 90 degree.

The term "hydrophobic", "non-wetting", or "does not wet" of a surface means that the contact angle of a sample on the surface is equal to or larger than 90 degree.

The term "variation" of a quantity refers to the difference between the actual value and the desired value or the average of the quantity. And the term "relative variation" of a quantity refers to the ratio of the variation to the desired value or the average of the quantity. For example, if the desired value of a quantity is Q and the actual value is (Q+□), then the □/(Q+□) is the relative variation. The term "relative sample thickness variation" refers to the ratio of the sample thickness variation to the average sample thickness.

The term "optical transparent" refers to a material that allows a transmission of an optical signal, wherein the term "optical signal" refers to, unless specified otherwise, the optical signal that is used to probe a property of the sample, the plate, the spacers, the scale-marks, any structures used, or any combinations of thereof.

The term "none-sample-volume" refers to, at a closed configuration of a CROF process, the volume between the plates that is occupied not by the sample but by other objects that are not the sample. The objects include, but not limited to, spacers, air bubbles, dusts, or any combinations of thereof. Often none-sample-volume(s) is mixed inside the sample.

The term "saturation incubation time" refers to the time needed for the binding between two types of molecules (e.g. capture agents and analytes) to reach an equilibrium. For a surface immobilization assay, the "saturation incubation time" refers the time needed for the binding between the target analyte (entity) in the sample and the binding site on plate surface reaches an equilibrium, namely, the time after which the average number of the target molecules (the entity) captured and immobilized by the binding site is statistically nearly constant.

In some cases, the "analyte" and "binding entity" and "entity" are interchangeable.

The term "first plate" and "collection plate are interchangeable. The term "second plate" and "cover plate" are interchangeable.

A "processor," "communication device," "mobile device," refer to computer systems that contain basic electronic elements (including one or more of a memory, input-output interface, central processing unit, instructions, network interface, power source, etc.) to perform computational tasks. The computer system may be a general purpose computer that contains instructions to perform a specific task, or may be a special-purpose computer.

A "site" or "location" as used in describing signal or data communication refers to the local area in which a device or subject resides. A site may refer to a room within a building structure, such as a hospital, or a smaller geographically defined area within a larger geographically defined area. A remote site or remote location, with reference to a first site that is remote from a second site, is a first site that is physically separated from the second site by distance and/or by physical obstruction. The remote site may be a first site that is in a separate room from the second site in a building structure, a first site that is in a different building structure from the second site, a first site that is in a different city from the second site, etc.

As used herein, the term "sample collection site" refers to a location at which a sample may be obtained from a subject. A sample collection site may be, for example, a retailer location (e.g., a chain store, pharmacy, supermarket, or department store), a provider office, a physician's office, a hospital, the subject's home, a military site, an employer site, or other site or combination of sites. As used herein, the term "sample collection site" may also refer to a proprietor or representative of a business, service, or institution located at, or affiliated with, the site.

As used herein, "raw data" includes signals and direct read-outs from sensors, cameras, and other components and instruments which detect or measure properties or characteristics of a sample.

"Process management," as used herein, refers to any number of methods and systems for planning and/or monitoring the performance of a process, such as a sample analysis process.

One with skill in the art will appreciate that the present invention is not limited in its application to the details of construction, the arrangements of components, category selections, weightings, pre-determined signal limits, or the steps set forth in the description or drawings herein. The invention is capable of other embodiments and of being practiced or being carried out in many different ways.

1. Vapor Condensate Assay by Two Movable Plates without Using Spacers

One aspect of the present invention is that we developed and experimentally demonstrated of collecting and assaying vapor condensate (VC) (e.g. EBC samples) using a pair of movable plates without using spacers.

Exhaled breath condensate (EBC) analysis is a noninvasive method of detecting biomarkers, mainly coming from the lower respiratory tract. EBC is collected during quiet breathing, as a product of cooling and condensation of the exhaled aerosol.

An exemplary device and method of collecting exhaled breath condensate (EBC) using a SiEBC (single-drop exhaled breath condensate collector/analyzer) or SiVC (single-drop vapor condensate collector/analyzer) that does not have spacers, as illustrated in FIG. 1, comprises the basic steps:

(1) exhaling breath onto the collection plate (FIG. 1-1). A subject (e.g. human) breathe onto a plate, termed "collection plate", and the breath condenses into EBC, which are in droplets with different sizes, depending on the breathing time. For a short breathing time most droplets are separated from each other. The surface of the collection plate that collects the EBC is termed the sample surface;

(2) placing a cover plate over the collection plate and pressing them together (FIG. 1-2). A cover plate with spacers (which are used for regulating the spacing between the cover plate and the substrate plate) is placed on top of the sample surface; and (3) pressing plates into a "Closed-Configuration (FIG. 1-3). The cover plate and the substrate are compressed together with at least a part of the EBC between the plates.

In the method of FIG. 1, the initial droplets are pressed into a thin layer EBC of a thickness that is regulated by the plates and spacers (not shown).

One reason for using the wording of "single drop" in SiEBCA is that in principle, the SiEBCA can detect and analyze a single drop of EBC deposited on the plate.

In the description of the present invention, "the substrate plate" and "the cover plate" are respectively interchangeable with "the first plate" and "the second plate".

In some embodiments, the plates are cooled to reduce the evaporation of collected EBC.

AA0-1. A device for collecting and analyzing vapor condensate (VC) sample, comprising:
 a collection plate and a cover plate, wherein:
 i. the plates are movable relative to each other into different configurations;
 ii. one or both plates are flexible; and
 iii. each of the plates has, on its inner respective surface, a sample contact area for contacting a vapor condensate (VC) sample that contains an analyte;
 wherein one of the configurations is an open configuration, in which: the two plates are either completely or partially separated apart, and the VC sample is deposited on one or both of the plates; and
 wherein another of the configurations is a closed configuration which is configured after the VC sample deposition in the open configuration; and in the closed configuration: at least a part of the VC sample is between the two plates and in contact with the two plates, and has a thickness that (a) is regulated by the two sample contact surfaces of the plates without using spacers, and (b) is equal to or less than 30 □m with a small variation.

AA0-2 Another device is provided herein for collecting and analyzing vapor condensate (VC) sample, comprising:
 a collection plate and a cover plate, wherein:
 i. the plates are movable relative to each other into different configurations;
 ii. one or both plates are flexible; and
 iii. each of the plates has, on its respective surface, a sample contact area for contacting a vapor condensate (VC) sample that contains an analyte;
  wherein one of the configurations is an open configuration, in which: the two plates are either completely or partially separated apart, and the VC sample is deposited on one or both of the plates; and
  wherein another of the configurations is a closed configuration which is configured after the VC sample deposition in the open configuration; and in the closed configuration: at least a part of the VC sample is between the two plates and in contact with the two plates, and has a thickness that is regulated by the plate spacing without using spacers.

In some embodiments, the thickness of the sample in a closed configuration of the plates is measured. The sample thickness in a plate closed configuration include Fabry-Pérot interferometer, or different optical focusing methods, or others.

Experiment-1

In an experiment by the present invention, an exemplary SiEBCA device comprises a collection plate of 25 mm×25 mm×1 mm PMMA planar plate with untreated surfaces, and a cover plate of 25 mm×25 mm×0.175 mm PMMA planar plate with bare untreated surfaces. The EBC sample was collected by having a subject breathe on a collection plate for 2 sec and a cover plate was immediately brought to cover the collection plate and pressed against it as described above. Later, the SiEBCA together with the sample collected therein were subject to optical measurement and microscopy imaging.

FIG. 6 Schematically Illustrates the Optical Measurement and Imaging Taken for the Measurement of the EBC Sample Thickness and Lateral Area, Respectively.

As shown in panel (A), Fabry-Pérot interferometer was used to measure the F-P cavity resonance in the reflectance spectra at 25 points on the 4×4 grid artificially generated in the center of the SiEBCA device, from which the plate spacing (and the sample thickness) is thus deduced. Each of the 25 measuring points is about 2 um by 2 um in area, and all 25 points cover an area of 20 mm by 20 mm. An average plate spacing over the 25 points was taken as the estimate of the sample thickness ($\widetilde{T_{EBC}}$). As shown in panel (B), a direct photo of the SiEBCA device was taken to delineate the general contour of the EBC sample between the two plates and measure the overall lateral area ($S_t$). Then microscopic images were taken at each of the 25 points (each image covers an area $S_i$ of 1.6 mm×1.1 mm), and then these images were analyzed by an image processing software to recognize and measure the total area of the air bubbles ($S_b$) in each image.

To estimate the total EBC sample lateral area, first, the percentage of EBC liquid lateral area ($a_i$) for each measuring point is calculated as $(S_i-S_b)/S_i \times 100\%$; second, an average value (ã) is taken from all 25 points; and finally, the total EBC sample lateral area ($S_{EBC}$) is estimated as $S_t*$ã.

The volume of the EBC sample ($V_{EBC}$) is thus determined as $S_{EBC} * \widetilde{T_{EBC}}$.

Figure 7:
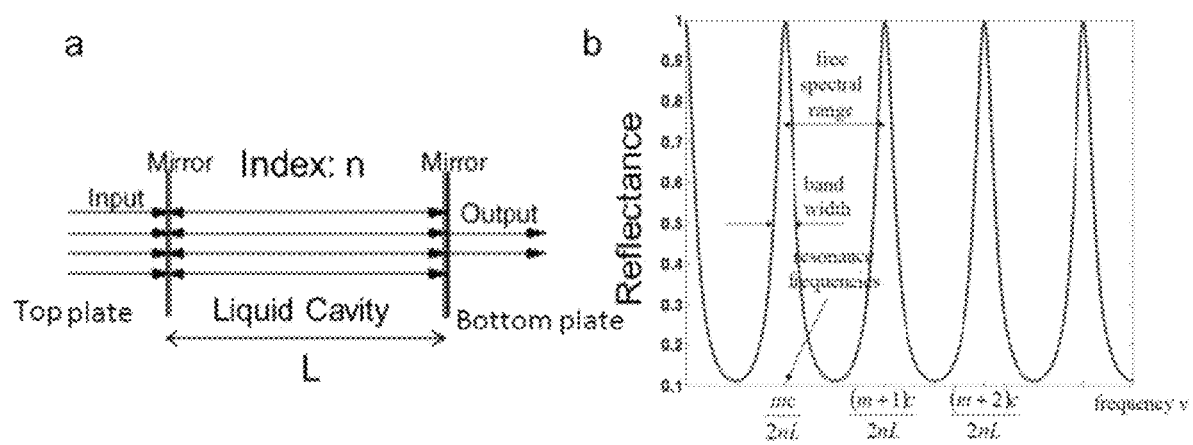
FIG. 7 demonstrates the principle of plate spacing measurement based on F-P cavity resonance.

FIG. 7 Demonstrates the Principle of Plate Spacing Measurement Based on F-P Cavity Resonance.

Panel (a) shows the schematic of F-P cavity from the SiEBCA device; panel (b) shows the typical reflectance spectrum and resonances from the device. The plate spacing (h) at each measuring point is calculated as:

$$h = \frac{c}{2n\Delta v}$$

where h is the plate spacing, c is light speed, $\Delta v$ is the period in frequency domain and n is the reflective index of the EBC liquid.

As described above, the average EBC sample thickness is equal to $$\frac{\sum_1^{25} h}{25}.$$

EBC sample thickness uniformity is calculated as $$\sqrt{\frac{\sum_1^{25}(h-H)^2}{25}}.$$

Figure 8:
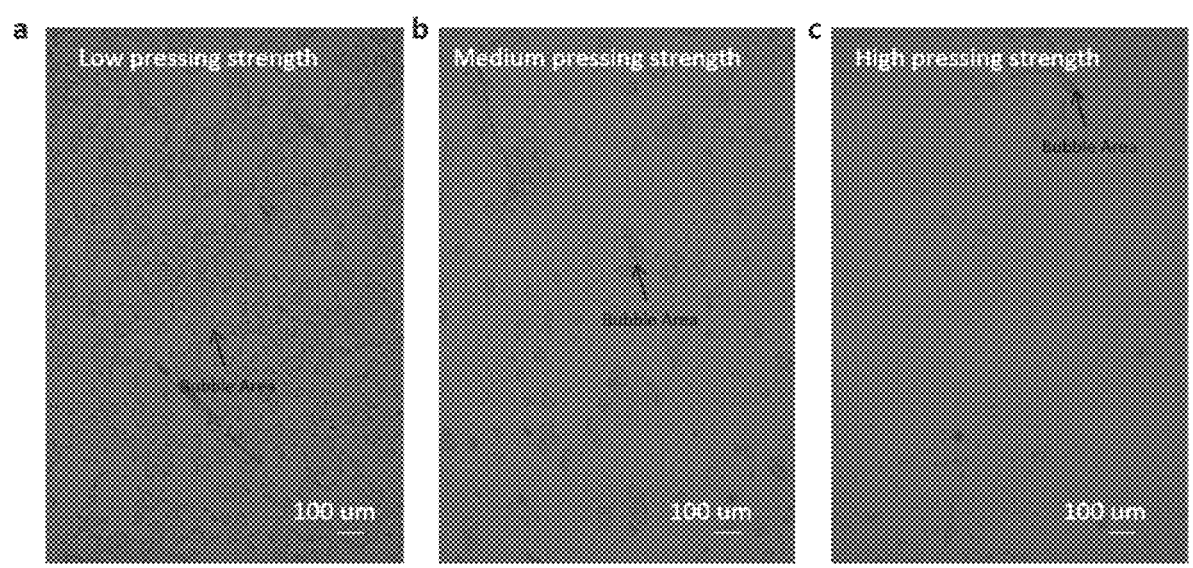
FIG. 8 shows microscopic images of the EBC sample collected using the exemplary SiEBCA device without spacers.

FIG. 8 Shows Microscopic Images of the EBC Sample Collected Using the Exemplary SiEBCA Device without Spacers.

Panels (a)-(b) respectively show the images of the EBC samples at the closed configuration after hand pressing the two plates with low, medium, and high pressing strength. Low strength was less than 10 kg, high strength was higher than 15 kg, and medium strength was in between the low and high strength.

Under these three different conditions, the performance of the exemplary SiEBCA device without spacers was examined and summarized in Table 3, based on the measurement and calculation methods described above. As shown in Table 3 and FIG. 8, low strength gives thicker liquid thickness with larger bubble area, while high strength gives thinner EBC sample layer with smaller bubble area.

TABLE 3

Performance of SiEBCA without spacers

| | Press Strength | Average EBC area percentage ã | EBC Area $S_{EBC}$ (mm²) | Average EBC thickness $\widetilde{T_{EBC}}$ (um) | Collected EBC volume $V_{EBC}$ (uL) | EBC thickness uniformity |
|---|---|---|---|---|---|---|
| 1 | Low | 38% | 240 | 1.45 | 0.35 | 58% |
| 2 | Medium | 72% | 450 | 0.87 | 0.39 | 47% |
| 3 | High | 98% | 620 | 0.51 | 0.32 | 43% |

2. Vapor Condensate Assay by Two Movable Plates with Spacers

AA1-1 In some embodiments, as illustrated in FIG. 1 (2), a device is provided herein for collecting and analyzing vapor condensate (VC) sample, comprising:
   a collection plate, a cover plate, and spacers, wherein:
   i. the plates are movable relative to each other into different configurations;
   ii. one or both plates are flexible;
   iii. each of the plates has, on its respective inner surface, a sample contact area for contacting a vapor condensate (VC) sample that contains an analyte;
   iv. the spacers are fixed to the respective inner surface of one or both of the plates, and have a predetermined substantially uniform height and a predetermined constant inter-spacer distance and wherein at least one of the spacers is inside the sample contact area;
      wherein one of the configurations is an open configuration, in which: the two plates are either completely or partially separated apart, the spacing between the plates is not regulated by the spacers, and the VC sample is deposited on one or both of the plates; and
      wherein another of the configurations is a closed configuration which is configured after the VC sample deposition in the open configuration; and in the closed configuration: at least a part of the VC sample is between the two plates and in contact with the two plates, and has a highly uniform thickness that is regulated by the spacers and the two sample contact surfaces of the plates and is equal to or less than 30 □m.

3. Different Embodiments for Devices with or without Spacers

In some embodiments, the device further comprises, on one or both plates, one or a plurality of dry binding sites and/or one or a plurality of reagent sites. In some embodiments, the sample is exhale breath condensate.

In some embodiments, the sample is a vapor from a biological sample, an environmental sample, a chemical sample, or clinical sample. In some embodiments, wherein the analyte comprises a molecule (e.g., a protein, peptides, DNA, RNA, nucleic acid, or other molecules), cells, tissues, viruses, and nanoparticles with different shapes. In some embodiments, wherein the analyte comprises volatile organic compounds (VOCs). In some embodiments, wherein the analyte comprises nitrogen, oxygen, $CO_2$, $H_2O$, and inert gases. In some embodiments, wherein the analyte is stained.

In some embodiments, the device may comprise a dry reagent coated on one or both of the plates. In some embodiments, the dry reagent may bind to an analyte in the blood an immobilize the analyte on a surface on one or both of the plates. In these embodiments, the reagent may be an antibody or other specific binding agent, for example. This dry reagent may have a pre-determined area. In other embodiments, the device may comprise a releasable dry reagent on one or more of the plates, e.g., a labeled reagent such as a cell stain or a labeled detection agent such as an antibody or the like. In some cases, there may be a release time control material on the plate that contains the releasable dry reagent, wherein the release time control material delays the time that the releasable dry regent is released into the blood sample.

In some cases, the release time control material delays the time that the dry regent is released into the blood sample by at least 3 seconds, e.g., at least 5 seconds or at least 10 seconds. Some embodiments, the drive may contain multiple dry binding sites and/or multiple reagent sites, thereby allowing multiplex assays to be performed. In some cases, the areas occupied by the drying binding sites may oppose the areas occupied by the reagent sites when the plates are in the closed position.

In some embodiments, the regent comprises labeling or staining reagent(s).

In some embodiments, the spacers regulating the layer of uniform thickness (i.e., the spacers that are spacing the plates away from each other in the layer) have a "filling factor" of at least 1%, e.g., at least 2% or at least 5%, wherein the filling factor is the ratio of the spacer area that is in contact with the layer of uniform thickness to the total plate area that is in contact with the layer of uniform thickness. In some embodiments, for spacers regulating the layer of uniform thickness, the Young's modulus of the spacers times the filling factor of the spacers is equal or larger than 10 MPa, e.g., at least 15 MPa or at least 20 MPa, where the filling factor is the ratio of the spacer area that is in contact with the layer of uniform thickness to the total plate area that is in contact with the layer of uniform thickness. In some embodiments, the thickness of the flexible plate times the Young's modulus of the flexible plate is in the range 60 to 750 GPa-um, e.g., 100 to 300 GPa-um, 300 to 550 GPa-um, or 550 to 750 GPa-um. In some embodiments, for a flexible plate, the fourth power of the inter-spacer-distance (ISD) divided by the thickness of the flexible plate (h) and the Young's modulus (E) of the flexible plate, $ISD4/(hE)$, is equal to or less than $10^6$ um3/GPa, e.g., less than $10^5$ um3/GPa, less then $10^4$ um3/GPa or less than $10^3$ um3/GPa.

In some embodiments, one or both plates comprises a location marker either on a surface of or inside the plate, that provide information of a location of the plate, e.g., a location that is going to be analyzed or a location onto which the blood should be deposited. In some cases, one or both plates may comprise a scale marker, either on a surface of or inside the plate, that provides information of a lateral dimension of a structure of the blood sample and/or the plate. In some embodiments, one or both plates comprises an imaging marker, either on surface of or inside the plate that assists an imaging of the sample. For example, the imaging marker could help focus the imaging device or direct the imaging device to a location on the device. In some embodiments, the spacers can function as a location marker, a scale marker, an imaging marker, or any combination of thereof.

In some embodiments, on one of the sample surface, it further comprises an enclosure-spacer that encloses a partial or entire VC samples deposited on the collection plate.

In some embodiments, the highly uniform thickness has a value equal to or less than 0.5 um. In some embodiments, the highly uniform thickness has a value in the range of 0.5 um to 1 um, 1 um to 2 um, 2 um to 10 um, 10 um to 20 um or 20 um to 30 um.

In some embodiments, the thickness of the at least a part of VC sample at the closed configuration is larger than the thickness of VC sample deposited on the collection plate at an open configuration.

In some embodiments, the thickness of the at least a part of VC sample at the closed configuration is less than the thickness of VC sample deposited on the collection plate at an open configuration.

In some embodiments, wherein the spacers are fixed on a plate by directly embossing the plate or injection molding of the plate.

In some embodiments, wherein the materials of the plate and the spacers are selected from polystyrene, PMMA, PC, COC, COP, or another plastic.

In some embodiments, the inter-spacer spacing in the range of 1 um to 50 um, 50 um to 100 um, 100 um to 200 um or 200 um to 1000 um.

In some embodiments, the VC sample is an exhaled breath condensate from a human or an animal.

In some embodiments, the spacers regulating the layer of uniform thickness have a filling factor of at least 1%, wherein the filling factor is the ratio of the spacer area in contact with the layer of uniform thickness to the total plate area in contact with the layer of uniform thickness.

In some embodiments, for spacers regulating the layer of uniform thickness, the Young's modulus of the spacers times the filling factor of the spacers is equal or larger than 10 MPa, wherein the filling factor is the ratio of the spacer area in contact with the layer of uniform thickness to the total plate area in contact with the layer of uniform thickness.

In some embodiments, for a flexible plate, the thickness of the flexible plate times the Young's modulus of the flexible plate is in the range 60 to 750 GPa-um.

In some embodiments, for a flexible plate, the fourth power of the inter-spacer-distance (ISD) divided by the thickness of the flexible plate (h) and the Young's modulus (E) of the flexible plate, $ISD4/(hE)$, is equal to or less than $10^6$ um3/GPa, In some embodiments, one or both plates comprises a location marker, either on a surface of or inside the plate, that provide information of a location of the plate.

In some embodiments, one or both plates comprises a scale marker, either on a surface of or inside the plate, that provide information of a lateral dimension of a structure of the sample and/or the plate.

In some embodiments, one or both plates comprises an imaging marker, either on surface of or inside the plate, that assists an imaging of the sample.

In some embodiments, the spacers functions as a location marker, a scale marker, an imaging marker, or any combination of thereof.

In some embodiments, the average thickness of the layer of uniform thickness is about equal to a minimum dimension of an analyte in the sample.

In some embodiments, the inter-spacer distance is 1 μm or less, 5 μm or less, 7 μm or less, 10 μm or less, 20 μm or less, 30 μm or less, 40 μm or less, 50 μm or less, 60 μm or less, 70 μm or less, 80 μm or less, 90 μm or less, 100 μm or less, 200 μm or less, 300 μm or less, 400 μm or less, or in a range between any two of the values.

In some embodiments, the inter-spacer distance is substantially periodic.

In some embodiments, the inter-spacer distance is aperiodic.

In some embodiments, the spacers are pillars with a cross-sectional shape selected from round, polygonal, circular, square, rectangular, oval, elliptical, or any combination of the same.

In some embodiments, the spacers have are pillar shape and have a substantially flat top surface, wherein, for each spacer, the ratio of the lateral dimension of the spacer to its height is at least 1.

In some embodiments, each spacer has the ratio of the lateral dimension of the spacer to its height is at least 1.

In some embodiments, the minimum lateral dimension of spacer is less than or substantially equal to the minimum dimension of an analyte in the sample.

In some embodiments, the minimum lateral dimension of spacer is in the range of 0.5 um to 100 um.

In some embodiments, the minimum lateral dimension of spacer is in the range of 0.5 um to 10 um.

In some embodiments, the spacers have a density of at least 100/mm2. In some embodiments, the spacers have a density of at least 1000/mm2. In some embodiments, at least one of the plates is transparent.

In some embodiments, at least one of the plates is made from a flexible polymer.

In some embodiments, for a pressure that compresses the plates, the spacers are not compressible and/or, independently, only one of the plates is flexible.

In some embodiments, the flexible plate for the device of any prior embodiment has a thickness in the range of 10 um to 200 um. In some embodiments, the plate thickness is 0.5 um, 1 um, 5 um, 10 um, 25 um, 50 um, 75 um, 100 um, 125 um, 150 um, 175 um, 200 um, 250 um, or a range between any of the two values.

In some embodiments, the variation in the thickness of the at least a part of the sample in a closed configuration of the plates is less than 30%, 10%, 5%, 3% or 1%.

In some embodiments, the first and second plates are connected and are configured to be changed from the open configuration to the closed configuration by folding the plates.

In some embodiments, the first and second plates are connected by a hinge and are configured to be changed from the open configuration to the closed configuration by folding the plates along the hinge.

In some embodiments, the first and second plates are connected by a hinge that is a separate material to the plates, and are configured to be changed from the open configuration to the closed configuration by folding the plates along the hinge In some embodiments, the first and second plates are made in a single piece of material and are configured to be changed from the open configuration to the closed configuration by folding the plates.

In some embodiments, the layer of uniform thickness sample is uniform over a lateral area that is at least 100 um'.

In some embodiments, the layer of uniform thickness sample is uniform over a lateral area that is at least 1 mm$^2$.

In some embodiments, the device is configured to analyze the sample in 60 seconds or less.

In some embodiments, at the closed configuration, the final sample thickness device is configured to analyze the sample in 60 seconds or less.

In some embodiments, the device is configured to analyze the sample in 180 seconds or less.

In some embodiments, at the closed configuration, the final sample thickness device is configured to analyze the sample in 180 seconds or less.

In some embodiments, the device further comprises, on one or both of the plates, one or a plurality of amplification sites that are each capable of amplifying a signal from the analyte or a label of the analyte when the analyte or label is within 500 nm from an amplification site.

In some embodiments, at the closed configuration, the final sample thickness device is configured to analyze the sample in 10 seconds or less.

In certain embodiments, the device of any prior embodiment include a step of amplifying the signal from the sample while being in a device that is in a closed configuration of the plates. The signal amplification is achieved without the use of by a physical process and/or biological/chemical amplification. Biological/chemical amplification of the signal include enzymatic amplification of the signal (e.g., used in enzyme-linked immunosorbent assays (ELISAs)) and polymerase chain reaction (PCR) amplification of the signal. The physical signal amplification include plamonics, proximity dependent surface amplification by metal structures or films, and others.

In some embodiments, the dry binding site comprises a capture agent.

In some embodiments, the dry binding site comprises an antibody or nucleic acid. In some embodiments, the releasable dry reagent is a labeled reagent. In some embodiments, the releasable dry reagent is a fluorescently-labeled reagent. In some embodiments, the releasable dry reagent is a dye. In some embodiments, the releasable dry reagent is a beads. In some embodiments, the releasable dry reagent is a quantum dot. In some embodiments, the releasable dry reagent is a fluorescently-labeled antibody.

In some embodiments, the first plate further comprises, on its surface, a first predetermined assay site and a second predetermined assay site, wherein the distance between the edges of the assay site is substantially larger than the thickness of the uniform thickness layer when the plates are in the closed position, wherein at least a part of the uniform thickness layer is over the predetermined assay sites, and wherein the sample has one or a plurality of analytes that are capable of diffusing in the sample.

In some embodiments, the first plate has, on its surface, at least three analyte assay sites, and the distance between the edges of any two neighboring assay sites is substantially larger than the thickness of the uniform thickness layer when the plates are in the closed position, wherein at least a part of the uniform thickness layer is over the assay sites, and wherein the sample has one or a plurality of analytes that are capable of diffusing in the sample.

In some embodiments, the first plate has, on its surface, at least two neighboring analyte assay sites that are not separated by a distance that is substantially larger than the thickness of the uniform thickness layer when the plates are in the closed position, wherein at least a part of the uniform thickness layer is over the assay sites, and wherein the sample has one or a plurality of analytes that are capable of diffusing in the sample.

In some embodiments, the releasable dry reagent is a cell stain. In some embodiments, the device further comprises a detector that is an optical detector for detecting an optical signal. In some embodiments, the device further comprises a detector that is an electrical detector for detecting an electric signal.

In some embodiments, the device comprises discrete spacers that are not fixed to any of the plates, wherein at the closed configuration, the discrete spacers are between the inner surfaces of the two plates, and the thickness of the sample is confined by the inner surfaces of the two plates, and regulated by the discrete spacers and the plates.

In some embodiments, the device further comprises a binding site that has a chemical sensor that is made from a material selected from the group consisting of: silicon nanowire (Si NW); single-walled carbon nanotubes (SWCNT); random networks of carbon nanotubes (RN-CNTs); molecularly capped metal nanoparticles (MCNPs); metal oxide nanoparticles (MONPs); and chemically sensitive field-effect transistors (CHEM-FETs).

A system is provided herein for rapidly analyzing a vapor condensate sample using a mobile phone comprising:
 (a) a device of any prior embodiments;
 (b) a mobile communication device comprising:
  i. one or a plurality of cameras for the detecting and/or imaging the vapor condensate sample; and
  ii. electronics, signal processors, hardware and software for receiving and/or processing the detected signal and/or the image of the vapor condensate sample and for remote communication.

In some embodiments, the system further comprise a light source from either the mobile communication device or an external source.

In some embodiments, one of the plates has a binding site that binds an analyte, wherein at least part of the uniform sample thickness layer is over the binding site, and is substantially less than the average lateral linear dimension of the binding site.

In some embodiments, the system further comprising:
 (d) a housing configured to hold the sample and to be mounted to the mobile communication device.

In some embodiments, the housing comprises optics for facilitating the imaging and/or signal processing of the sample by the mobile communication device, and a mount configured to hold the optics on the mobile communication device.

In some embodiments, an element of the optics in the housing is movable relative to the housing.

In some embodiments, the mobile communication device is configured to communicate test results to a medical professional, a medical facility or an insurance company.

In some embodiments, the mobile communication device is further configured to communicate information on the test and the subject with the medical professional, medical facility or insurance company.

In some embodiments, the mobile communication device is further configured to communicate information of the test to a cloud network, and the cloud network process the information to refine the test results.

In some embodiments, the mobile communication device is further configured to communicate information of the test and the subject to a cloud network, the cloud network process the information to refine the test results, and the refined test results will send back the subject.

In some embodiments, the mobile communication device is configured to receive a prescription, diagnosis or a recommendation from a medical professional.

In some embodiments, the mobile communication device is configured with hardware and software to:
 a. capture an image of the sample;
 b. analyze a test location and a control location in in image; and
 c. compare a value obtained from analysis of the test location to a threshold value that characterizes the rapid diagnostic test.

In some embodiments, at least one of the plates comprises a storage site in which assay reagents are stored. In some embodiments, at least one of the cameras reads a signal from the CROF device. In some embodiments, the mobile communication device communicates with the remote location via a wifi or cellular network.

In some embodiments, the mobile communication device is a mobile phone.

A method is provided herein for rapidly analyzing an analyte in a sample using a mobile phone, comprising:
 a) depositing a sample on the device of any prior embodiment;
 b) assaying an analyte in the sample deposited on the device to generate a result; and
 c) communicating the result from the mobile communication device to a location remote from the mobile communication device.

In some embodiments, the analyte comprises a molecule (e.g., a protein, peptides, DNA, RNA, nucleic acid, or other molecule), cells, tissues, viruses, and nanoparticles with different shapes.

In some embodiments, the analyte comprises white blood cell, red blood cell and platelets. In some embodiments, the method comprises:
 a. analyzing the results at the remote location to provide an analyzed result; and
 b. communicating the analyzed result from the remote location to the mobile communication device.

In some embodiments, the analysis is done by a medical professional at a remote location. In some embodiments, the mobile communication device receives a prescription, diagnosis or a recommendation from a medical professional at a remote location.

In some embodiments, the thickness of the at least a part of VC sample at the closed configuration is larger than the thickness of VC sample deposited on the collection plate at an open configuration.

In some embodiments, the thickness of the at least a part of VC sample at the closed configuration is less than the thickness of VC sample deposited on the collection plate at an open configuration.

In some embodiments, the assaying step comprises detecting an analyte in the sample.

In some embodiments, the analyte is a biomarker. In some embodiments, the analyte is a protein, nucleic acid, cell, or metabolite. In some embodiments, the assay done in step (b) is a binding assay or a biochemical assay.

A method is provided herein for analyzing an analyte in a vapor condensate sample comprising:

obtaining a device of any prior device claim;

depositing the vapor condensate sample onto one or both pates of the device;

placing the plates in a closed configuration and applying an external force over at least part of the plates; and analyzing the analyts in the layer of uniform thickness while the plates are the closed configuration.

In some embodiments, the method comprises:

(a) obtaining a sample;

(b) obtaining a first and second plates that are movable relative to each other into different configurations, wherein each plate has a sample contact surface that is substantially planar, one or both plates are flexible, and one or both of the plates comprise spacers that are fixed with a respective sample contacting surface, and wherein the spacers have:

i. a predetermined substantially uniform height,
 ii. a shape of pillar with substantially uniform cross-section and a flat top surface;
 iii. a ratio of the width to the height equal or larger than one;
 iv. a predetermined constant inter-spacer distance that is in the range of 10 um to 200 um;
 v. a filling factor of equal to 1% or larger; and (c) depositing the sample on one or both of the plates when the plates are configured in an open configuration, wherein the open configuration is a configuration in which the two plates are either partially or completely separated apart and the spacing between the plates is not regulated by the spacers;

(d) after (c), using the two plates to compress at least part of the sample into a layer of substantially uniform thickness that is confined by the sample contact surfaces of the plates, wherein the uniform thickness of the layer is regulated by the spacers and the plates, and has an average value equal to or less than 30 um with a variation of less than 10%, wherein the compressing comprises:

bringing the two plates together; and
 conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and (e) analyzing the in the layer of uniform thickness while the plates are the closed configuration;

wherein the filling factor is the ratio of the spacer contact area to the total plate area;

wherein a conformable pressing is a method that makes the pressure applied over an area is substantially constant regardless the shape variation of the outer surfaces of the plates; and wherein the parallel pressing applies the pressures on the intended area at the same time, and a sequential pressing applies the pressure on a part of the intended area and gradually move to other area.

In some embodiments, the method comprises removing the external force after the plates are in the closed configuration; and imaging the analytes in the layer of uniform thickness while the plates are the closed configuration; and counting a number of analytes or the labels in an area of the image.

In some embodiments, the method comprises removing the external force after the plates are in the closed configuration; and measuring optical signal in the layer of uniform thickness while the plates are the closed configuration.

In some embodiments, the inter-spacer distance is in the range of 20 um to 200 um. In some embodiments, the inter-spacer distance is in the range of 5 um to 20 um.

In some embodiments, a product of the filling factor and the Young's modulus of the spacer is 2 MPa or larger.

In some embodiments, the surface variation is less than 50 nm.

In some embodiments, the method further comprising a step of calculating the concentration of an analyte in the relevant volume of sample, wherein the calculation is based on the relevant sample volume defined by the predetermined area of the storage site, the uniform sample thickness at the closed configuration, and the amount of target entity detected.

In some embodiments, the analyzing step comprise counting the analyte in the sample. In some embodiments, the imaging and counting is done by:

i. illuminating the cells in the layer of uniform thickness;
 ii. taking one or more images of the cells using a CCD or CMOS sensor;
 iii. identifying cells in the image using a computer; and
 iv. counting a number of cells in an area of the image.

In some embodiments, the external force is provided by human hand. In some embodiments, the method future comprises a dry reagent coated on one or both plates.

In some embodiments, the layer of uniform thickness sample has a thickness uniformity of up to +/−5%.

In some embodiments, the spacers are pillars with a cross-sectional shape selected from round, polygonal, circular, square, rectangular, oval, elliptical, or any combination of the same.

In some embodiments, the spacing between the spacers is approximately the minimum dimension of an analyte.

The method of any prior embodiment, wherein one or both plate sample contact surfaces comprises one or a plurality of amplification sites that are each capable of amplifying a signal from the analyte or a label of the analyte when the analyte or label is within 500 nm from an amplification site.

In some embodiments, the sample is exhale breath condensate. In some embodiments, the sample is a vapor from a biological sample, an environmental sample, a chemical sample, or clinical sample. In some embodiments, the analyte comprises a molecule (e.g., a protein, peptides, DNA, RNA, nucleic acid, or other molecules), cells, tissues, viruses, and nanoparticles with different shapes In some embodiments, the analyte comprises volatile organic compounds (VOCs). In some embodiments, the analyte comprises nitrogen, oxygen, $CO_2$, $H_2O$, and inert gases. In some embodiments, the analyte is stained.

In some embodiments, on one of the sample surface, it further comprises an enclosure-spacer that encloses a partial or entire VC samples deposited on the collection plate. In some embodiments, the highly uniform thickness has a value equal to or less than 0.5 um. In some embodiments, the highly uniform thickness has a value in the range of 0.5 um to 1 um. In some embodiments, the highly uniform thickness has a value in the range of 1 um to 2 um. In some embodiments, the highly uniform thickness has a value in the range of 2 um to 10 um. In some embodiments, the highly uniform thickness has a value in the range of 10 um to 20 um. In some embodiments, the highly uniform thickness has a value in the range of 20 um to 30 um.

In some embodiments, on one of the sample surface, it further comprises an enclosure-spacer that encloses a partial or entire VC samples deposited on the collection plate.

Embodiment (EBC)-1. SiEBCA (Single-Drop Exhaled Breath Condensate Collector and Analyzer)

Exhaled breath condensate (EBC) analysis is a noninvasive method of detecting biomarkers, mainly coming from the lower respiratory tract. EBC is collected during quiet breathing, as a product of cooling and condensation of the exhaled aerosol.

An exemplary method of collecting exhaled breath condensate (EBC) using a SiEBCA (Single-drop EBC Collector/Analyzer), as illustrated in FIG. 1, comprises the basic steps:

(1) exhaling breath onto the collection plate (FIG. 1-1). A subject (e.g. human) breathe onto a plate, termed "collection plate", and the breath condenses into EBC, which are in droplets with different sizes, depending on the breathing time. For a short breathing time most droplets are separated from each other. The surface of the collection plate that collects the EBC is termed the sample surface;

(2) placing a cover plate over the collection plate and pressing them together (FIG. 1-2). A cover plate with spacers (which are used for regulating the spacing between the cover plate and the substrate plate) is placed on top of the sample surface; and (3) pressing plates into a "Closed-Configuration (FIG. 1-3). The cover plate and the substrate are compressed together with at least a part of the EBC between the plates.

In the method of FIG. 1, the initial droplets are pressed into a thin layer EBC of a thickness that is regulated by the plates and spacers (not shown).

One reason for using the wording of "single drop" in SiEBCA is that in principle, the SiEBCA can detect and analyze a single drop of EBC deposited on the plate.

In the description of the present invention, "the substrate plate" and "the cover plate" are respectively interchangeable with "the first plate" and "the second plate".

In some embodiments, the plates are cooled to reduce the evaporation of collected EBC.

A1 A method of collecting EBC, as a basic embodiment of the present invention for collecting EBC from a subject, as illustrated in FIG. 1, comprises the steps:

(a) obtaining a collection plate and a cover plate that are movable relative to each other into different configurations, wherein one or both of the plates comprise spacers (not shown in FIG. 1 but in FIG. 2) that are fixed with the respective plate, and have a predetermined average height of 100 um or less;

(b) depositing, when the plates are configured in an open configuration, an EBC sample by exhaling breath from a subject toward the collection plate, wherein:

(i) the exhaled breath condensates on a collection surface of the collection plate to form droplets and/or puddles that have different lateral sizes and different heights, depending upon the surface wetting properties of the collection surface; and (ii) the open configuration is a configuration in which the two plates are either partially or completely separated apart and the spacing between the plates is not regulated by the spacers; and (c) after (b), bringing the cover plate over the collection surface of the collection plate and then bringing the two plates into a closed configuration by pressing the plates, wherein:

(i) the closed configuration is a configuration, in which: at least a part of the spacers are between the cover plate and the collection plate, and a relevant area of the collection surface of the collection plate is covered by the cove plate and has a plate spacing that is regulated by the spacers; and (ii) at the closed configuration, in the relevant area, substantial number or all of the droplets or puddles formed in step (b) at the open configuration merge into puddle(s) that (1) have much larger lateral size but in a smaller number than the open configuration and (2) touch both inner surfaces of the cover plate and the collection plate, thereby the thickness of the puddle(s) is confined by the inner surfaces of the plates and equal to the spacing between the inner surfaces, and the total surface area of the deposited EBC exposed to the ambient is significantly reduced;

wherein the plate spacing is the spacing between the two inner surfaces (the two surfaces facing each other) of the cover plate and the collection plate, the relevant area is a portion or entire surface of the collection surface, and the collection surface is a portion or entire surface of the collection plate.

From our experiments (described in details in Examples), we found that the final form of the EBC collected by SiEBCA when the plates are in the closed configuration depends upon the spacer height. Experimentally, we found, as illustrated in FIG. 2, that:

(1) At the closed configuration of the SiEBCA, if the spacing between the inner surfaces of the plates is less than the average height of the EBC droplets or puddles at the open configuration, the EBC droplets or puddles are compressed by the collection plate and the cover plate into a continuous film of a thickness thinner than at the open configuration, and also air pockets may exist in the film; and (2) otherwise (i.e. if the spacing is equal to or larger than that the average height at the open configuration) the droplets and/or puddles self-emerged into discrete puddles that are fewer in number but larger in lateral size (area) than that in the open configuration, touch both sample contact (inner) surfaces of the cover plate and the collection plate, and have the thickness confined by the inner surfaces of the plates and equal to the spacing between the inner surfaces. In this case, the EBC sample thickness at the closed configuration is equal to or larger than the EBC sample average thickness at the open configuration. The increase in the EBC puddle thickness at the closed configuration, as we observed experimentally, are due to the interactions between the plates and the EBC sample.

EBC-1.2. Device for EBC Collection

FIG. 4. is an illustration of an embodiment of the devices and the methods of a SiEBCA (Single-drop EBC Collector/Analyzer): (a) having a first plate and a second plate, wherein one or both plate has spacers (shown here: only the first plate has spacers); (b) depositing a sample (only one of many EBC droplets is shown) on the first plate (shown), or the second plate (not shown), or both (not shown) at an open configuration; and (c) (i) using the two plates to spread the sample (the sample flow between the plates) and reduce the sample thickness, and (ii) using the spacers and the plate to regulate the sample thickness at the closed configuration.

A2 A device of collecting EBC, as a basic embodiment of the present invention for collecting EBC sample from a subject, as illustrated in FIG. 1, comprises:
  i. a first plate and a second plate, wherein the plates are movable relative to each other into different configurations, and one or both plates are flexible;
  ii. a sample contact area on the respective surface of each of the plates for contacting EBC sample,
  iii. spacers on one or both of the plates, wherein the spacers are fixed with a respective plate, have a predetermined substantially uniform height of 30 um or less and a predetermined constant inter-spacer distance that is 250 um or less, and wherein at least one of the spacers is inside the sample contact area;
  wherein one of the configurations is an open configuration, in which: the two plates are separated apart, the spacing between the plates is not regulated by the spacers, and the EBC sample is deposited on one or both of the plates from a subject; and
  wherein another of the configurations is a closed configuration which is configured after the EBC sample deposition in the open configuration; and in the closed configuration: at least part of the EBC sample is compressed by the two plates into a layer of highly uniform thickness, wherein the uniform thickness of the layer is in contact with and confined by the inner surfaces of the two plates and is regulated by the plates and the spacers.

In some embodiments of paragraphs A1 and A2, the deposition of the EBC sample is by directly exhaling from a subject to one of the plates.

In some embodiments of paragraphs A1 and A2, the deposition of the EBC sample is by directly exhaling from a subject to both of the plates.

"Covering time delay" means a time period that it takes from the step (b) EBC deposition of paragraph A1 to the end of the step (c) of paragraph A1 that brings the cover plate and the collection plate to a closed configuration.

In the method of paragraph A1, the covering time delay should be as short as possible to reduce the evaporation of deposited EBC. In one preferred embodiment, the covering time delay is equal to or less than 2 sec. In another preferred embodiment, the covering time delay is equal to or less than 5 sec. In another preferred embodiment, the covering time delay is equal to or less than 10 sec. In another preferred embodiment, the covering time delay is equal to or less than 30 sec. And In another preferred embodiment, the covering time delay is in the range of 30 sec to 300 sec (e.g. 30 to 60 sec, 60 sec to 120 sec, or 120 sec to 300 sec).

EBC-1.3. Significant Reduction of EBC Evaporation Rate.

One key advantage of the method and device of paragraph A1 and A2 is that, compared to the open configuration of the collection plate and the cover plate, the closed configuration of the plates significantly reduces the surface area of the EBC exposed to the ambient, and hence significantly reduces the EBC sample evaporation rate and significantly increases the time that EBC sample is in liquid form (i.e. the time that EBC sample is not completely evaporated). For example, we have observed that the drying time (the time it takes for the EBC sample to dry out completely) increased from 30 secs at an open configuration to 70 mins, a factor of 140 times longer.

EBC-1.4. Guard Ring (Enclosed Spacers).

To further reduce the EBC sample evaporation rate, the enclosed spacers or the guard rings can be used to surround the sample to seal off the sample from the ambient. The guard ring can circle an area that is the same as, or larger or smaller than the EBC sample deposited at the open configuration. The guard ring can be configured to further divide an EBC sample into multiple chambers (FIG. 5).

Figure 5B:
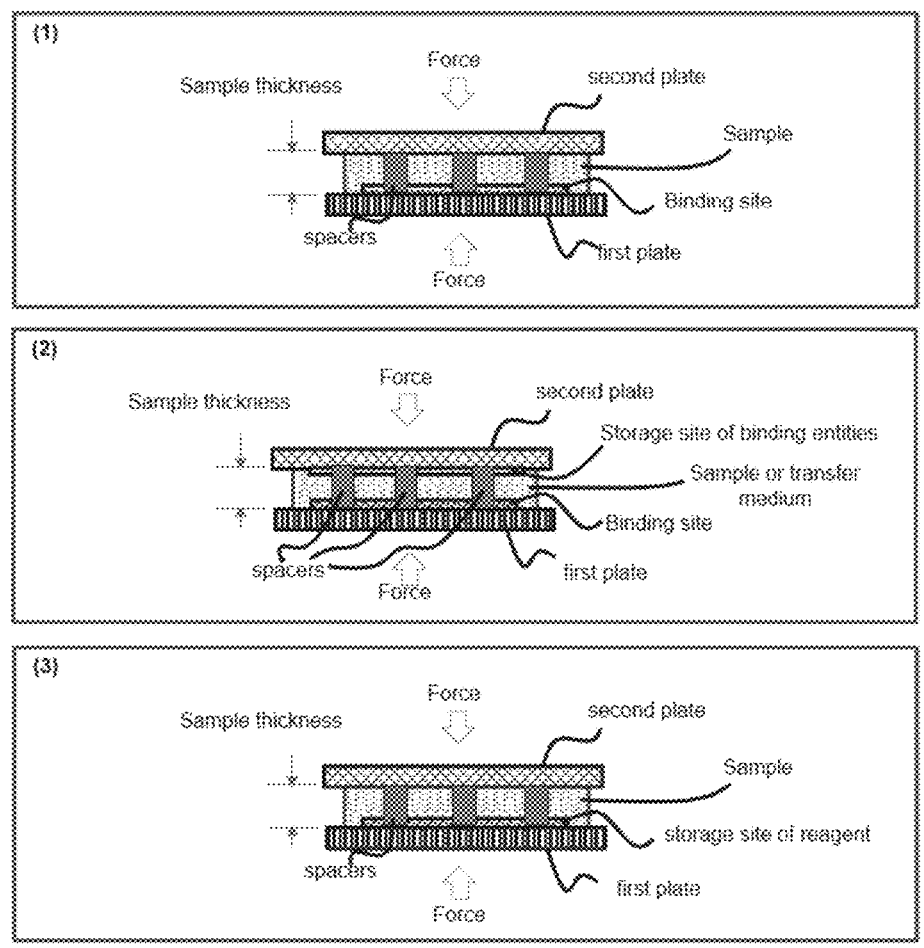
FIG. 5b shows reducing binding or mixing time by reducing the sample thickness using two pates, spacers, and compression (shown in cross-section). Panel (1) illustrates reducing the time for binding entities in a sample to a binding site on a solid surface (X-(Volume to Surface)). Panel (2) illustrates reducing the time for binding entities (e.g. reagent) stored on a surface of plate to a binding site on a surface of another surface (X-(Surface to Surface)). Panel (3) illustrates reducing the time for adding reagents stored on a surface of a plate into a sample that is sandwiched between the plate and other plate (X-(Surface to Volume)).

FIG. 5 is an illustration of a SiEBCA with both "open spacer" and enclosed spacer, where the open spacer is a post (pillar) while the enclosed spacer is a ring. The enclosed spacer reduces the evaporation of the EBC collected inside the enclosed spacer, since at the closed configuration, the enclosed spacer, the cover plate and the collection plate form an enclosed chamber. If there are only the open spacers but not an enclosed spacer, at the plate closed configuration, the collected EBC still evaporates from the edge of the film formed by the EBC, although such evaporation is much slower than that without a cover plate.

In the method and the device of paragraph A1 and A2, the spacers can be an open spacer(s), an enclosed spacer(s), or a combination of thereof.

Details of the devices and methods to keep the EBC thickness uniform are given in the other part of the disclosure.

Embodiment EBC-2. EBC Analysis

A-3 A method of analyzing EBC from a subject for analyzing EBC of a subject comprising:
(a) obtaining a device of any prior embodiments;
(b) depositing, when the plates are configured in an open configuration, an EBC sample by exhaling breath from a subject toward the collection plate, wherein:
  (i) the exhaled breath condensates on a collection surface of the collection plate to form droplets and/or puddles that have different lateral sizes and different heights, depending upon the surface wetting properties of the collection surface; and
  (ii) the open configuration is a configuration in which the two plates are either partially or completely separated apart and the spacing between the plates is not regulated by the spacers;
(c) after (b), bringing the cover plate over the collection surface of the collection plate and then bringing the two plates into a closed configuration by pressing the plates, wherein:
  (i) the closed configuration is a configuration, in which: at least a part of the spacers are between the cover plate and the collection plate, and a relevant area of the collection surface of the collection plate is covered by the cove plate and has a plate spacing that is regulated by the spacers; and
  (ii) at the closed configuration, in the relevant area, substantial number or all of the droplets or puddles formed in step (b) at the open configuration merge into puddle(s) that (1) have much larger lateral size but in a smaller number than the open configuration and (2) touch both inner surfaces of the cover plate and the collection plate, thereby the thickness of the puddle(s) is confined by the inner surfaces of the plates and equal to the spacing between the inner surfaces, and the total surface area of the deposited EBC exposed to the ambient is significantly reduced; and
(d) analyzing the EBC,
  wherein the plate spacing is the spacing between the two inner surfaces (the two surfaces face each other) of the cover plate and the collection plate, the relevant area is a portion or entire surface of the collection surface, and the collection surface is a portion or entire surface of the collection plate.

The collection plate generally is held at a temperature the same as the ambient, but in some embodiments, the temperatures can be different from the ambient, either higher or lower depending upon the goal of the collection. For example, a temperature lower than the ambient may be used for reducing the EBC evaporation; and a temperature higher than the ambient many bused for evaporating more than that at the ambient temperature is needed.

The present invention provides that EBC samples and the target analytes therein can be analyzed by a variety of analysis techniques, depending on the sample volume, species and abundance of the target analyte(s). A non-exhaustive and mutually non-exclusive list of these analysis techniques include spectrometry (e.g., mass spectrometry (MS), ion mobility spectrometry, proton transfer spectrometry, optical absorption spectroscopy systems, and spectrofluorimetry), enzyme based techniques, immunoassay methods (e.g., ELISA, radioimmunoassay, and immune sensors), electronic noses, 2-dimensional protein gel electrophoresis (2D-PEG) followed by chromatographic proteomic microanalysis, nucleic acid (including amplification by PRC (polymerase chain reaction) and isothermal amplification of nucleic acid) by and various types of chemical sensors.

4. Additional Exemplary Analysis by SiVC with or without Spacers

Another significant advantage of the present invention is that the method and the device of paragraph A1-2, in some embodiments, are used as an EBC analyzer by itself directly or with certain modifications. The EBC analyzer analyzes one or a plurality of target analytes in the EBC. The target analytes are further discussed in Section 3.

In some embodiments, the modifications made to the method and device of paragraphs A1-A2 include, but not limited to, the following, which can used alone (individually) or in combinations:
  (1) Binding Sites. One or both of the plates have one or plurality of binding site . . . . Each (type) of the reagents are in either in well separated locations (the well separation will be defined later).
  (2) Storage sites. One or both of the plates have one or plurality of binding site . . . . Each (type) of the regents are in either in well separated locations (the well separation will be defined later).
  (3) Amplification site.
  (4) Multiplexing of analyte detections.

More details of the binding sites, storage sites, amplification sites, and multiplexing sites, as well as their usage for VC and EBC analysis are given in the other part of the disclosure.

In addition to the various embodiments detailed in other parts of the disclosure, in some embodiments, the modifications made to the method and the device of paragraphs A1-A2 included the use of chemical sensors as binding agents in the binding site for sensing target analytes in the EBC sample, in particular VOC compounds. These chemical sensors include, but not limited to. sensors based on conducting polymers and metal oxides, surface acoustic wave sensors, and optical sensors. In some embodiments, they involve the use of nanotechnology (gold nanoparticles, nanowires, and nanotubes) for the design of VOC sensors. In some embodiments, the chemical sensors give output in the forms of color change, fluorescence, conductivity, vibration, sound, or any combination thereof, following the interaction of the VOC compound with the sensor.

In particular embodiments, the chemical sensor is made from materials, including, but not limited to, silicon nanowire (Si NW); single-walled carbon nanotubes (SWCNT); random networks of carbon nanotubes (RN-CNTs); molecularly capped metal nanoparticles (MCNPs); metal oxide nanoparticles (MONPs); and chemically sensitive field-effect transistors (CHEM-FETs) that are respectively functionalized for the detection of VOCs or other analytes in the EBC sample. The term "functionalization" (or "functionalized") as used herein refer to the modification to (or the modified properties of) a material that enables it to have specific interaction (e.g., binding, chemical reaction) with certain type(s) of target analytes and bring about a signal indicative of such interaction, thereby to sense the existence and/or abundance of the target analyte. The term "functional group" as used herein refers to the chemical group that is chemically or physically coupled to the material that functionalizes the material.

In some embodiments, the functional group is made from a protein, an amino acid, a nucleic acid, a lipid, a carbohydrate, a metabolite, any other organic compound, or any other inorganic compound that is able to interact with target analyte in the EBC sample.

In the art of EBC detection, in particular the sampling/sensing of the VOC compound, it is challenging to achieve high selectivity against individual components of the sample. Many available reagents (sensors, e.g., a particular type of chemical sensor or functional group, or a particular antibody) are not particularly sensitive to one type of target analytes, rather selective to a certain range of target analytes. A solution to this is to utilize an array of different cross-reactive sensors in couple with data processing system capable of pattern recognition to virtually separate and identify individual components based on the output pattern/parameters of the sensors. The term "cross-reactive" as used herein refers to the fact that a number of reagents/sensors are selectively responsive to a respective range of analytes and the responsive range of each reagent/sensor overlaps partially with at least one of the other reagents/sensors.

In some embodiments, the device and method of paragraphs A1-A2 include a variety of reagents (sensors), many of which are cross-reactive, and the device and method are utilized in conjunction with a data processing system, including both hardware and software that are capable of pattern recognition. In particular, the data processing methods embodied by the data processing system include, but not limited to, principal component analysis, cluster analysis, discriminant function analysis, genetic algorithms, neutral network algorithms, and any other machine learning algorithms.

In some other embodiments, the method and device of prior embodiments are used for collecting EBC samples for analysis by other EBC analyzer(s) according to any of the aforementioned analysis techniques or any combination thereof.

Another advantage of the method and device of prior embodiments a is that the volume of the collected sample is ready to be quantified, or it is easy to quantitatively collect a pre-determined volume of sample for further analysis. As detailed in other part of the disclosure, in some embodiments, a continuous film of the sample is formed after bringing the plates in to the closed configuration. The relevant volume of sample is therefore readily and precisely determined by timing the relevant area by the thickness of the sample film, which is equal to the plate spacing. In some embodiments, the plate spacing is equal to or deviating with a small variation from the spacer height. In some embodiments, the spacers have a uniform height, and the sample film has a uniform thickness equal to the uniform height.

In some embodiments, the analyzing step of paragraph A0 to A3 comprises: 1) at the closed configuration, taking a first volume of the sample having a first lateral area out of the sample collected in between the cover plate and the collection plate; 2) analyzing the first volume of the sample by an analyzer. As discussed above, the first volume of the sample is equal to the product of the first lateral area and the plate spacing. In some embodiments, the first lateral area is pre-determined or pre-known. For instance, the device features visual marks that define or border a certain area on the cover plate, the collection plate, or both, within the overlapping area between the two plates, and the first volume of sample is taken according to the marks, e.g., by cutting out along the marks. In this case, the sample needs to be a continuous film with no or little empty space within the boundary set by the visual marks. In some embodiments, the first lateral area is measured during or after the taking step.

In some other embodiments, the EBC samples collected according to the method and device of paragraphs A1-A2 are analyzed by a combination of both the EBC device itself and other analyzers.

Embodiment EBC-3. Exemplary Applications of SiVC/SiEBC

EBC-3.1. Analysis of EBC

Breath tests are among the least invasive methods available for clinical diagnosis, disease state monitoring, health monitoring and environmental exposure assessment.

EBC analysis can be used for detection of inflammatory markers, which reflect the state of chronic airways diseases such as chronic obstructive pulmonary disease (COPD), asthma, and cystic fibrosis (CF). EBC analysis can also be used for identification of metabolic, proteomic, and genomic fingerprints of breathing, aiming for an early diagnosis of not only respiratory, but also systemic diseases.

A breath matrix from a subject is a mixture of nitrogen, oxygen, CO2, H2O, and inert gases. The remaining small fraction consists of more than 1000 trace volatile organic compounds (VOCs) with concentrations in the range of parts per million (ppm) to parts per trillion (ppt) by volume. In terms of their origin, these volatile substances may be generated in the body (endogenous) or may be absorbed as contaminants from the environment (exogenous). The composition of VOCs in breath varies widely from person to person, both qualitatively and quantitatively.

Although the number of VOCs found to date in human breath is more than 1000, only a few VOCs are common to all humans. These common VOCs, which include isoprene, acetone, ethane, and methanol, are products of core metabolic processes and are very informative for clinical diagnostics. The bulk matrix and trace VOCs in breath exchange between the blood and alveolar air at the blood-gas interface in the lung. One exception is NO, which is released into the airway in the case of airway inflammation.

The endogenous compounds found in human breath, such as inorganic gases (e.g., NO and CO), VOCs (e.g., isoprene, ethane, pentane, acetone), and other typically nonvolatile substances such as isoprostanes, peroxynitrite, or cytokines, can be measured in breath condensate. Testing for endogenous compounds can provide valuable information concerning a possible disease state. Furthermore, exogenous molecules, particularly halogenated organic compounds, can indicate recent exposure to drugs or environmental pollutants.

Volatile Organic Compounds (VOCs) are organic substances that have a high vapor pressure and therefore evaporate at room temperature. The VOCs that may be assayed as target analytes by the methods and devices provided by the present invention include, but not limited to, biologically generated VOCs (e.g., terpenes, isoprene, methane, green leaf volatiles) and anthropogenic VOCs (e.g., typical solvents used in paints and coatings, like ethyl acetate, glycol ethers, and acetone, vapors from adhesives, paints, adhesive removers, building materials, etc., like methylene chloride, MTBE, and formaldehyde, chlorofurocarbons and perchloroethylene used in dry cleaning, vapor and exhaustive gas from fossil fuels, like benzene and carbon monoxide).

Detailed discussion on certain breath markers for diseases and other health conditions is given in Table 1.

Besides the diseases listed in Table 1, various VOCs contained in exhaled breath have also been linked to different types of cancers. A non-exclusive list of breath VOCs identified as biomarkers for cancers is shown in Table 2.

Besides some of the non-volatile compounds listed in Table 1, various non-volatile compounds have also been lined to or identified as biomarkers of various diseases/conditions. Among these, a particular application of the device and method provided by the present disclosure is to assay the glucose level in EBC. Other applications include, but not limited to, detecting the levels of nitrogen reactive species, arachidonic acid metabolites (e.g., isoprostanes, leukotrienes, prostanoids), cytokines, glutathione, proteins and metabolites, small molecules (e.g., chloride, sodium, potassium, urea, and small organic acids), and pH.

In some embodiments, the devices and methods of the present invention also find applications in the detection of drugs of abuse in EBC sample. The drugs of abuse to be detected using the devices and methods of the present invention include, but not limited to, ethanol, *cannabis*, methadone, amphetamine, methamphetamine, 3,4-methylenedioxymethamphetamine, codeine, 6-acetylmorphine, diazepam, oxazepam, morphine, benzoylecgonine, cocaine, buprenorphine and tetrahydrocannabinol.

TABLE 1

Breath markers in certain diseases or conditions

| Disease/Condition | Breath Marker |
| --- | --- |
| Diabetes/diabetic ketoacidosis | Acetone, Ethylbenzene, Xylene, Touluene, Ethane, Pentane, Propane, Isoprene, Ethanol, Methanol, Isopropanol, 2,3,4-Trimethylhexane, 2,6,8-Trimethyldecane, Tridecane, Undecane |
| Helicobacter pylori infection | Ammonia, volatile organic compounds |
| Uremia/kidney failure | Dimethylamine, trimethylamine |
| Liver disease | Dimethylamine, trimethylamine |
| Liver disease | Ethanethiol, dimethylsulfide, hydrogen disulfide |
| Liver cirrhosis | Acetone, styrene, dimethylsulfide, dimethylselene |
| Liver disease/fetor hepaticus | C2-C5 Aliphatic acids, methylmercaptan |

TABLE 1-continued

Breath markers in certain diseases or conditions

| Disease/Condition | Breath Marker |
| --- | --- |
| Angina, ischemic heart disease | Alkanes, methylated alkanes |
| Heart-transplant rejection | Methylated alkane contour |
| Rheumatoid arthritis | Pentane |
| Allograft rejection | CS2 |
| Oxidative stress | NO, CO, nitrosothiol, 8-isoprostane, 4-hydroxy-2-nonenal, malondialdehyde, hydrogen peroxide |
| Chronic obstructive pulmonary disease | NO, CO, nitrosothiol, hydrogen peroxide |
| Rhinitis, rhinorrhea chronic cough | NO |
| Asthma | Pentane, ethane, 8-isoprostane, NO, pH, H2O2, leukotrienes (e.g., LTs, Cys-LTs, LTE4), 8-Isoprostane, PGE2, ILs, IL-4, IL-5, IL-6, IL-8, IL-10, IL-17, INF-☐, RANTES, MIP☐, MIP☐, TNF-☐, TGF-☐, ET-1, Cytokeratine 1, MDA, ADMA, CCL11, hs-CRP, sICAM-1 |
| Cystic fibrosis | NO, CS2, leukotrienes (e.g., LTE4), pH, Nitrotyrosine, Nitrites, Nitric oxide, 8-Isoprostane, IL-6, IL-8, IL-5, TNF-☐ |
| Bronchiectasis | NO |
| Lung cancer | Alkanes, monomethylated alkanes, nitric oxide |
| Lung carcinoma | Acetone, methylethylketone, n-propanol, alkanes, aniline, o-toluidine |
| Breast cancer | 2-propanol, 2,3-dihydro-1-4(1H)-quinazolinone, 1-phenyl-ethanone, heptanal, isopropyl myristate |
| Idiopathic pulmonary fibrosis (IPF) | 8-Isoprostane, H2O2, 3-nitrotyrosine, NOx, docosatetraenoyl-LPA |
| Pulmonary arterial hypertension (PAH) | Natriuretic peptide, pro-BNP, ET-1, 6-keto-PGF1α, 8-isoprostane, IL-6 |
| Sarcoidosis | 8-Isoprostane, Cys-LTs, Neopterin, TGF-☐ |
| Obstructive SleepApnea Syndrome (OSA) | |
| Pediatric patients | 8-Isoprostane, IL-6, LTB4, Cys-LTs, H2O2, Uric salts |
| Adult patients | 8-Isoprostane, IL-6, TNF-☐, pH, H2O2, ICAM-1, IL-8 |
| Systemic Lupus Erythematosus (SLE) | IL-6, IL-8, IL-10 |
| Chronic Renal Disease (CRD) | pH, Nitrites, Nitrates, H2O2 |

TABLE 2

VOCs from exhaled breath that are identified in biomarkers of various cancers

| Disease | Compound name |
| --- | --- |
| Lung cancer | 1,3-Cyclopentadiene, 1-methyl-<br>1-Cyclopentene<br>2,3-Butanedione<br>2-Butanol, 2,3-dimethyl-<br>2-Butanone (methyl ethyl ketone)<br>2-Butanone, 3-hydroxy-<br>2-Butene, 2-methyl-<br>3-Butyn-2-ol<br>Acetophenone<br>Benzaldehyde<br>Benzene, cyclobutyl-<br>Butane, 2-methyl-<br>Butyl acetate<br>Ethylenimine<br>Isoquinoline, 1,2,3,4-tetrahydro-<br>Methyl propyl sulfide<br>n-Pentanal<br>n-Undecane<br>Undecane, 3,7-dimethyl-<br>Urea, tetramethyl-<br>Cyclopentane<br>Acetone<br>Methyl ethyl ketone<br>n-Propanol<br>1,1'-(1-Butenylidene)bis benzene<br>1-Methyl-4-(1-methylethyl)benzene<br>2,3,4-Trimethyl hexane<br>3,3-Dimethyl pentane<br>Dodecane |

TABLE 2-continued

VOCs from exhaled breath that are identified in biomarkers of various cancers

| Disease | Compound name |
|---|---|
| | 1,3-Butadiene, 2-methyl-(isoprene) |
| | 1-Heptene |
| | 1-Hexene |
| | Benzene |
| | Benzene, 1,2,4-trimethyl- |
| | Benzene, 1,4-dimethyl |
| | Benzene, 1-methylethenyl- |
| | Benzene, propyl- |
| | Cyclohexane |
| | Cyclopentane, methyl- |
| | Cyclopropane, 1-methyl-2-pentyl- |
| | Decane |
| | Heptane, 2,2,4,6,6-pentamethyl |
| | Heptane, 2,4-dimethyl |
| | Heptane, 2-methyl |
| | Hexanal |
| | Methane, trichlorofluoro- |
| | Nonane, 3-methyl- |
| | Octane, 3-methyl- |
| | Styrene (ethenylbenzene) |
| | Undecane |
| | Butane |
| | Decane, 5-methyl |
| | Heptane |
| | Hexane, 2-methyl |
| | Hexane, 3-methyl |
| | Octane, 4-methyl |
| | Pentane |
| | Tridecane, 3-methyl |
| | Tridecane, 7-methyl |
| | 1,1-Biphenyl, 2,2-diethyl- |
| | 1,2-Benzenedicarboxylic acid, diethyl ester |
| | 1,5,9-Cyclododecatriene, 1,5,9-trimethyl- |
| | 10,11-Dihydro-5H-dibenz[b,f]azepine |
| | 1H-Indene, 2,3-dihydro-1,1,3-trimethyl-3-phenyl- |
| | 1-Propanol |
| | 2,4-Hexadiene, 2,5-dimethyl- |
| | 3-Pentanone, 2,4-dimethyl- |
| | 2,5-Cyclohexadiene-1,4-dione, 2,6-bis(1,1-dimethylethyl)- |
| | Benzene, 1,1-oxybis- |
| | Benzoic acid, 4-ethoxy-, ethyl ester |
| | Decane, 4-methyl- |
| | Furan, 2,5-dimethyl- |
| | Pentan-1,3-dioldiisobutyrate, 2,2,4-trimethyl |
| | Propanoic acid, 2-methyl-, 1-(1,1-dimethylethyl)-2-methyl-1,3-propanediyl ester |
| | trans-Caryophyllene |
| | 1,2,4,5-Tetroxane, 3,3,6,6-tetraphenyl- |
| | 1H-Indene, 2,3-dihydro-4-methyl- |
| | 1-Propene, 1-(methylthio)-, (E)- |
| | 2,2,4-Trimethyl-1,3-pentanediol diisobutyrate |
| | 2,2,7,7-Tetramethyltricyclo-[6.2.1.0(1,6)]undec-4-en-3-one |
| | 2,3-Hexanedione |
| | 2,5-Cyclohexadien-1-one, 2,6-bis(1,1-dimethylethyl)-4-ethylidene |
| | 2-Methyl-3-hexanone |
| | 4-Penten-2-ol |
| | 5,5-Dimethyl-1,3-hexadiene |
| | 5-Isopropenyl-2-methyl-7-oxabicyclo[4.1.0]heptan-2-ol |
| | 9,10-Anthracenediol, 2-ethyl- |
| | Anthracene, 1,2,3,4-tetrahydro-9-propyl- |
| | Benzene, 1,1-(1,2-cyclobutanediyl)bis,cis- |
| | Benzene, 1,1-[1-(ethylthio)propylidene]bis- |
| | Benzene, 1,1-ethylidenebis, 4-ethyl- |
| | Benzophenone |
| | Bicyclo[3.2.2]nonane-1,5-dicarboxylic acid, 5-ethyl ester |
| | Camphor |
| | Ethane, 1,1,2-trichloro-1,2,2-trifluoro- |
| | Furan, 2-[(2-ethoxy-3,4-dimethyl-2-cyclohexen-1-ylidene)methyl]- |
| | Isomethyl ionone |
| | Isopropyl alcohol |
| | Pentanoic acid, 2,2,4-trimethyl-3-carboxyisopropyl, isobutyl ester |
| | Propane, 2-methoxy-2-methyl- |
| | α-Isomethyl ionone |
| | Butanal |
| | Heptanal |
| | Nonanal |

TABLE 2-continued

VOCs from exhaled breath that are identified in biomarkers of various cancers

| Disease | Compound name |
|---|---|
| | Octanal |
| | Pentanal |
| | Propanal |
| | Ethylbenzene |
| | Octane |
| | Pentamethylheptane |
| | Toluene |
| | 2-Methylpentane |
| | Isoprene |
| | Xylenes total |
| | Styrene |
| | Aniline |
| | o-Toluidine |
| | 1-Butanol |
| | 3-Hydroxy-2-butanone |
| | 2,6,10-Trimethyltetradecane |
| | 2,6,11-Trimethyldodecane |
| | 2,6-Dimethylnaphthalene |
| | 2,6-Di-tert-butyl-, 4-methylphenol |
| | 2-Methylhendecanal |
| | 2-Methylnaphthalene |
| | 2-Pentadecanone |
| | 3,7-Dimethylpentadecane |
| | 3,8-Dimethylhendecane |
| | 4-Methyltetradecane |
| | 5-(1-Methyl)propylnonane |
| | 5-(2-Methyl)propylnonane |
| | 5-Butylnonane |
| | 5-Propyltridecane |
| | 7-Methylhexadecane |
| | 8-Hexylpentadecane |
| | 8-Methylheptadecane |
| | Eicosane |
| | Hexadecanal |
| | Nonadecane |
| | Nonadecanol |
| | Tridecane |
| | Tridecanone |
| | Formaldehyde (methanal) |
| | Isopropanol |
| Breast cancer | 2,3,4-Trimethyldecane |
| | 2-Amino-5-isopropyl-8-methyl-1-azulenecarbonitrile |
| | 3,3-Dimethyl pentane |
| | 5-(2-Methylpropyl)nonane |
| | 6-Ethyl-3-octyl ester 2-trifluoromethyl benzoic acid |
| | Nonane |
| | Tridecane, 5-methyl |
| | Undecane, 3-methyl |
| | Pentadecane, 6-methyl |
| | Propane, 2-methyl |
| | Nonadecane, 3-methyl |
| | Dodecane, 4-methyl |
| | Octane, 2-methyl |
| | 1-Phenylethanone |
| | 2,3-Dihydro-1-phenyl-4(1H)-quinazolinone |
| | 2-Propanol |
| | Heptanal |
| | Isopropyl myristate |
| | (+)-Longifolene |
| | 1,3-Butadiene, 2-methyl- |
| | 1,4-Pentadiene |
| | 1H-Cycloprop[e]azulene, decahydro-1,1,7-trimethyl-4-methylene- |
| | 1-Octanol, 2-butyl- |
| | 2,5-Cyclohexadiene-1,4-dione, 2,6-bis(1,1-dimethylethyl)- |
| | 2,5-Di-tert-butyl-1,4-benzoquinone |
| | 2-Hexyl-1-octanol |
| | 3-Ethoxy-1,1,1,5,5,5-hexamethyl-3-(trimethylsiloxy)trisiloxane |
| | Acetic acid, 2,6,6-trimethyl-3-methylene-7-(3-oxobutylidene)oxepan-2-yl ester |
| | Benzene, 1,2,3,5-tetramethyl- |
| | Benzene, 1,2,4,5-tetramethyl- |
| | Benzene, 1-ethyl-3,5-dimethyl- |
| | Benzoic acid, 4-methyl-2-trimethylsilyloxy-, trimethylsilyl ester |
| | Cyclohexene, 1-methyl-5-(1-methylethenyl)- |
| | Cyclohexene, 1-methyl-5-(1-methylethenyl)-, (R)- |
| | Cyclopropane, ethylidene |

TABLE 2-continued

VOCs from exhaled breath that are identified in biomarkers of various cancers

| Disease | Compound name |
|---|---|
| | Cyclotetrasiloxane, octamethyl- |
| | D-Limonene |
| | Dodecane |
| | Dodecane, 2,6,11-trimethyl- |
| | Dodecane, 2,7,10-trimethyl- |
| | Longifolene-(V4) |
| | Pentadecane |
| | Tetradecane |
| | Tridecane |
| | Trifluoroacetic acid, n-octadecyl ester |
| | Undecane |
| Colon cancer | 1,1'-(1-Butenylidene)bis benzene |
| | 1,3-Dimethylbenzene |
| | 4-(4-Propylcyclohexyl)-4'-cyano[1,1'-biphenyl]-4-yl ester benzoic acid |
| | 2-Amino-5-isopropyl-8-methyl-1-azulenecarbonitrile |
| | [(1,1-Dimethylethyl)thio]acetic acid |
| Esophagogastric cancer | Ethylphenol |
| | Hexanoic acid |
| | Methylphenol |
| | Phenol |
| Gastric cancer | 2-Butoxyethanol |
| | Isoprene |
| | 2-Propenenitrile |
| | 6-Methyl-5-hepten-2-one |
| | Furfural (furfuraldehyde) |
| Head and neck cancer | 4,6-Dimethyldodecane |
| | 5-Methyl-3-hexanone |
| | 2,2-Dimethyldecane |
| | Limonene |
| | 2,2,3-Trimethyl-exobicyclo[2.2.1]heptane |
| | 2,2-Dimethyl-propanoic acid |
| | Ammonium acetate |
| | 3-Methylhexane |
| | 2,4-Dimethylheptane |
| | 4-Methyloctane |
| | p-Xylene |
| | 2,6,6-Trimethyloctane |
| | 3-Methylnonane |
| Liver cancer | 3-Hydroxy-2-butanone |
| | Styrene |
| | Decane |
| Ovarian cancer | Decanal |
| | Nonanal |
| | Styrene |
| | 2-Butanone |
| | Hexadecane |
| Prostate cancer | Toluene |
| | p-Xylene |
| | 2-Amino-5-isopropyl-8-methyl-1-azulenecarbonitrile |
| | 2,2-Dimethyldecane |

EBC-3.2. Collection and Analysis of Other Vapor Condensates.

Certain embodiments of the present invention are related to the applications of the SiEBCA methods and devices for collection and analysis of the vapor condensates other than the EBC. The other moistures include, but not limited to, fog, clouds, steams, etc. The target analysis of these vapor condensates can be for different purpose environmental monitoring, emission control, etc. In some embodiments, the sample is a vapor from a biological sample, an environmental sample, a chemical sample, or clinical sample.

EBC-3.3. Automatic and High Throughput.

In certain embodiments, the devices and methods of the present invention are automatic and high speed, where the steps are performed by machines. In some embodiments, the plates are in the form of roll of sheets and are controlled by rollers to put certain area of the plates into an open configuration or a closed configuration.

EBC-3.4. Identification and Validation of Markers in Vapor Condensate

In certain embodiments, the devices and methods of the present invention are particularly useful for the identification and validation of biomarkers for human diseases/conditions, or other markers for environmental, food safety, or other conditions/events. Due to the ease, fast speed, small sample volume, and multiplexing potential of the present devices and methods, it is easy to adapt the present device for high-throughput and even automatic screening and validation of these markers. In certain embodiments, the present devices and methods are particularly useful when coupled with data processing system capable of pattern recognition for such purposes.

In certain embodiments, the devices and methods of the present invention are also advantageous to create large sample dataset for refining the algorithms for pattern recognition through machine learning and/or other methodologies.

EBC-4. EBC Collection and Analysis without Spacers

Another aspect of the present invention is to provide devices and methods for collecting and analyzing vapor condensate using the aforementioned collection plate and cover plate but without spacers.

In some embodiments of the present invention, the spacers that are used to regulate the sample or a relevant volume of the EBC sample are replaced by (a) positioning sensors that can measure the plate inner spacing, and/or (b) devices that can control the plate positions and move the plates into a desired plate inner spacing based on the information provided the sensors. In some embodiment, all the spacers are replaced by translation stage, monitoring sensors and feedback system.

In some embodiments, the collection plate and the cover plate comprise no spacers at all, and the EBC sample is compressed by the two plates into a thin layer, the thickness of which is regulated by the spacing between the inner surfaces of the plates (the plate spacing).

A4. A device for collecting EBC without spacers, comprises:
a first plate and a second plate, wherein:
  i. the plates are movable relative to each other into different configurations, and one or both plates are flexible;
  ii. both plates comprise a sample contact area on the respective surface of each plate for contacting EBC sample;
    wherein one of the configurations is an open configuration, in which: the two plates are separated apart, and the EBC sample is deposited on one or both of the plates from a subject; and
  wherein another of the configurations is a closed configuration which is configured after the EBC sample deposition in the open configuration; and in the closed configuration: at least part of the EBC sample is compressed by the two plates into a thin layer, wherein the thin layer is in contact with and confined by the inner surfaces of the two plates.

A5. A method of collecting EBC without spacers, comprises the steps:
  (a) obtaining a collection plate and a cover plate of paragraph A4;
  (b) depositing, when the plates are configured in the open configuration, an EBC sample by exhaling breath from a subject toward the collection plate, wherein the exhaled breath condensates on a collection surface of the collection plate to form droplets and/or puddles that have different lateral sizes and different heights, depending upon the surface wetting properties of the collection surface;
  (c) after (b), bringing the cover plate over the collection surface and then bringing the two plates into a closed configuration by pressing the plates, wherein at the closed configuration:
    (i) at least a part of the EBC sample is between the cover plate and the collection plate, and a relevant area of the collection surface of the collection plate is covered by the cove plate; and
    (ii) in the relevant area, a substantial number or all of the droplets or puddles formed in step (b) at the open configuration merge into puddle(s) that (1) have much larger lateral size but in a smaller number than the open configuration and (2) touch both inner surfaces of the cover plate and the collection plate, thereby the thickness of the puddle(s) is confined by the inner surfaces of the plates and equal to the spacing between the inner surfaces, and the total surface area of the deposited EBC exposed to the ambient is significantly reduced; and
  wherein the plate spacing is the spacing between the inner surfaces of the cover plate and the collection plate, the relevant area is a portion or entire surface of the collection surface, and the collection surface is a portion or entire surface of the collection plate.

A6. A method of analyzing EBC without spacers, comprises the steps:
  (a) obtaining a collection plate and a cover plate of paragraph A4;
  (b) depositing, when the plates are configured in the open configuration, an EBC sample by exhaling breath from a subject toward the collection plate, wherein the exhaled breath condensates on a collection surface of the collection plate to form droplets and/or puddles that have different lateral sizes and different heights, depending upon the surface wetting properties of the collection surface;
  (c) after (b), bringing the cover plate over the collection surface and then bringing the two plates into a closed configuration by pressing the plates, wherein at the closed configuration:
    (i) at least a part of the EBC sample is between the cover plate and the collection plate, and a relevant area of the collection surface of the collection plate is covered by the cove plate; and
    (ii) in the relevant area, a substantial number or all of the droplets or puddles formed in step (b) at the open configuration merge into puddle(s) that (1) have much larger lateral size but in a smaller number than the open configuration and (2) touch both inner surfaces of the cover plate and the collection plate, thereby the thickness of the puddle(s) is confined by the inner surfaces of the plates and equal to the spacing between the inner surfaces, and the total surface area of the deposited EBC exposed to the ambient is significantly reduced; and
  (d) analyzing the EBC,
  wherein the plate spacing is the spacing between the inner surfaces of the cover plate and the collection plate, the relevant area is a portion or entire surface of the collection surface, and the collection surface is a portion or entire surface of the collection plate.

In some embodiments, it is unlikely to obtain a layer of highly uniform thickness without using the spacers as discussed in the foregoing sessions. However, it is still advantageous to use the device and method of paragraphs A4-A5 for collecting and analyzing EBC sample, for it is easy, rapid to handle, requires no professional training and a very small volume of sample.

In some embodiments, the analyzing step (d) of paragraph A6 comprises determining the thickness of the collected EBC sample at the closed configuration after the formation of the thin layer during step (c). In some embodiments, the thickness of the collected EBC sample at the closed configuration is equal to the spacing between the inner surfaces of the two plates.

In some embodiments, measuring the spacing between the inner surfaces comprises the use of optical interference. The optical interference can use multiple wavelength. For example, the light signal due to the interference of a light reflected at the inner surface of the first plate and the second plate oscillate with the wavelength of the light. From the oscillation, one can determine the spacing between the inner surfaces. To enhance the interference signal, one of the inner surfaces or both can be coated with light reflection material.

In some embodiments, measuring the spacing between the inner surfaces comprises taking optical imaging (e.g. taking a 2D (two-dimensional)/3D (three-dimensional) image of the sample and the image taking can be multiple times with different viewing angles, different wavelength, different phase, and/or different polarization) and image processing.

In some embodiments, the analyzing step (d) of paragraph A6 comprises measuring the volume of the collected EBC sample based on the lateral area and the thickness of the thin layer that are determined after the formation of the thin layer during step (c).

In some embodiments, measuring the entire sample area or volume comprises taking optical imaging (e.g. taking a 2D (two-dimensional)/3D (three-dimensional) image of the sample and the image taking can be multiple times with different viewing angles, different wavelength, different phase, and/or different polarization) and image processing. The sample lateral area means the area in the direction approximately parallel to the first plate and the second plate. The 3D imaging can use the method of fringe projection profilometry (FPP), which is one of the most prevalent methods for acquiring three-dimensional (3D) images of objects.

In some embodiments, the measuring of the sample area or volume by imaging comprises: (a) calibration of the image scale by using a sample of the known area or volume (e.g., The imager is a smartphone and the dimensions of the image taken by the phone can be calibrated by comparing an image of the a sample of known dimension taken the same phone); (b) comparison of the image with the scale markers (rulers) placed on or near the first plate and second plate (discussed further herein), and (c) a combination of thereof.

As used herein, light may include visible light, ultraviolet light, infrared light, and/or near infrared light. Light may include wavelengths in the range from 20 nm to 20,000 nm.

In some embodiments, the pressing during step (c) of paragraphs A5-A6 is performed by human hand.

In some embodiments, the formation and properties of the thin layer is dependent on the pressing force applied during step (c) of paragraphs A5-A6 for bringing the two plates into the closed configuration (as demonstrated in EBC-6). In some embodiments, the pressing force applied during step (c) of paragraphs A5-A6 is well adjusted for forming a thin layer of EBC sample between the two plates that has prerequisite parameters.

EBC-5. More Examples of EBC Collection and Analysis Experiments

Additional exemplary experimental testing and observation, and additional preferred embodiments of the present invention are given.

All the exemplary experimental testing and demonstration of the present invention described in Section 4 (Examples) were performed under the following conditions and share the following common observations.

Plates.

Only one of the two plates of SiEBCA device, termed "X-Plate", has the spacers fixed on the sample surface of the plate, and the other plate, termed "the substrate plate", has a planar surface and does not have spacers. Unless particularly specified, the substrate plate was used as the collection plate, and the X-plate was used as the cover plate. Various materials (including glass, PMMA (polymethacrylate), and PS (polystyrene)) for the plates and various plate thicknesses have been tested. The planar surface of the plates typically have surface roughness less than 30 nm.

Spacers.

The spacers used on the X-Plate are rectangle pillars in a periodic array with a fixed inner spacer distance (ISD) and uniform spacer height. The pillar spacers have a straight sidewall with a tilt angle from the normal less than 5 degree. Different spacer height, size, inter-spacer distance, shape, and materials are tested.

Fabrication of Spacers.

The spacers are fabricated by nanoimprint on a plastic plate, where a mold is pressed directly into the plate. The mold was fabricated by lithography and etching. Examples of the spacers on the plate for SiEBCA. The spacers are fabricated by direct imprinting of the plastic plate surface using a mold, and has a dimension of width, length and height of 30 um, 40 um and 2 um.

EBC Sample Deposition.

All of the EBC samples were deposited on the collection plates by having a human subject directly exhale toward the collection plate which is placed within a few inches away from the subject's mouth.

The EBC samples depositions were performed in standard room conditions without any special temperature control or dust filters. We found that in our experiments, the dust does not affect to achieve the predetermined final sample thickness over a large sample area, and at the closed configuration the sample thickness over the non-dust area is regulated by the spacers. This demonstrated that the embodiments that we used for CROF performed to the results expected by the present invention.

Plate's Surface Wetting Properties.

Unless particularly specified, all the sample surfaces (i.e. the inner surface that contacts a sample) of the plates are untreated. We have tested the wetting properties of these untreated surfaces as a function of the plate material (glass, PMMA, and PS), the surface structures (planar or with spacers, and the sample type (water, PBS buffer and blood), by dropping a small drop of sample on the plate surface and measuring the sample to the plate contact angle. The wetting angles of the different surfaces for different samples were found experimentally as follows: For the liquid of water, PBS, and blood, the contact angle is about 46 degree for untreated glass, 60 degree for untreated PMMA surface, 60 degree for untreated PS (polystyrene) and about 61 degrees for untreated PMMA X-plate. Therefore they are all hydrophilic. But the wetting property of these surfaces can changed to either hydrophilic or hydrophobic by surface treatment. For a good vapor condensate collection, a hydrophilic surface is preferred, which will have, for a given amount of the condensation, smaller surface area by Hand-Press.

The present invention has performed various experiments in testing SiVC devices and methods, which are partially described in the PCT [Julia: Inset the info] (ESX-002PCT), which is incorporated herein for its entirety. Some of the experiments are summaried below (which used the device with spacers), but the present invention has preformed additional experiments and found that these observations are working for (and can bused) the SiVC device without spacers.

In all the experiment of the present invention, human hand(s) were the means to press a SiEBCA device (plates) into a closed configuration, which is referred as "hand-pressing".

Self-Holding.

Self-holding means that after a SiEBCA device (plates) is compressed into a closed configuration by an external force (e.g. the force from hand) and after the external force is removed, the SiEBCA device can hold, on its own, the sample thickness unchanged. We observed that in all the experiments in the Sec., all the SiEBCA devices and process (unless particularly specified) can self-hold, as demonstrated in the experiments. Our other experimental test showed that as long as one of the plate is hydrophilic, the SiEBCA plates can self-hold.

Drying speed with treated and untreated collection plates. For both experiments using treated and untreated collection plates, the drying speed of EBC was also calculated, which is defined as the retraction length per unit time of the edge of the liquid sample in the X-device at the closed configuration. The calculation shows that with the treated PMMA collection plate, the liquid sample dried at a slower speed (74 um/min) as compared to with the untreated PMMA collection plate (117 um/min).

Surface treatment. The surface treatment of the PMMA plate was performed with oxygen plasma, followed by deposition of 10 nm silicon oxide. In some embodiments, the treatment was performed chemically using trimethoxysilane.

AA2. The device of embodiment AA0 or AA1, wherein the device further comprises a dry reagent coated on one or both of the plates.

AA3. The device of any prior embodiment, wherein the device further comprises, on one or both plates, a dry binding site that has a predetermined area, wherein the dry binding site binds to and immobilizes an analyte in the sample.

AA4. The device of any prior embodiment, wherein the device further comprises, on one or both plates, a releasable dry reagent and a release time control material that delays the time that the releasable dry regent is released into the sample.

AA5. The device of embodiment 4, wherein the release time control material delays the time that the dry regent starts is released into the sample by at least 3 seconds.

AA6. The device of any prior embodiment, wherein the device further comprises, on one or both plates, one or a plurality of dry binding sites and/or one or a plurality of reagent sites.

AA7. The device of any prior embodiment, wherein the sample is exhale breath condensate.

AA8. The device of any prior embodiment, wherein the sample is a vapor from a biological sample, an environmental sample, a chemical sample, or clinical sample.

AA9. The device of any prior embodiment, wherein the analyte comprises a molecule (e.g., a protein, peptides, DNA, RNA, nucleic acid, or other molecules), cells, tissues, viruses, and nanoparticles with different shapes.

AA10. The device of any prior embodiment, wherein the analyte comprises volatile organic compounds (VOCs).

AA11. The device of any prior embodiment, wherein the analyte comprises nitrogen, oxygen, CO2, H2O, and inert gases.

AA12. The device of any prior embodiment, wherein the analyte is stained.

AA13. The device of any prior embodiment, wherein on one of the sample surface, it further comprises an enclosure-spacer that encloses a partial or entire VC samples deposited on the collection plate.

AA14. The device of any prior embodiment, wherein the highly uniform thickness has a value equal to or less than 0.5 um.

AA15. The device of any prior embodiment, wherein the highly uniform thickness has a value in the range of 0.5 um to 1 um.

AA16. The device of any prior embodiment, wherein the highly uniform thickness has a value in the range of 1 um to 2 um.

AA17. The device of any prior embodiment, wherein the highly uniform thickness has a value in the range of 2 um to 10 um.

AA18. The device of any prior embodiment, wherein the highly uniform thickness has a value in the range of 10 um to 20 um.

AA19. The device of any prior embodiment, wherein the highly uniform thickness has a value in the range of 20 um to 30 um.

AA20. The device of any prior embodiment, wherein the thickness of the at least a part of VC sample at the closed configuration is larger than the thickness of VC sample deposited on the collection plate at an open configuration.

AA21. The device of any prior embodiment, wherein the thickness of the at least a part of VC sample at the closed configuration is less than the thickness of VC sample deposited on the collection plate at an open configuration.

AA22. The device of any prior device embodiment, wherein the spacers are fixed on a plate by directly embossing the plate or injection molding of the plate.

AA23. The device of any prior device embodiment, wherein the materials of the plate and the spacers are selected from polystyrene, PMMA, PC, COC, COP, or another plastic.

AA24. The device of any prior embodiment, wherein the inter-spacer spacing is in the range of 1 um to 200 um.

AA25. The device of any prior embodiment, wherein the inter-spacer spacing is in the range of 200 um to 1000 um.

AA26. The device of any prior embodiment, wherein the VC sample is an exhaled breath condensate from a human or an animal.

AA27. The device of any prior embodiment, wherein the spacers regulating the layer of uniform thickness have a filling factor of at least 1%, wherein the filling factor is the ratio of the spacer area in contact with the layer of uniform thickness to the total plate area in contact with the layer of uniform thickness.

AA28. The device of any prior embodiment, wherein for spacers regulating the layer of uniform thickness, the Young's modulus of the spacers times the filling factor of the spacers is equal to or larger than 10 MPa, wherein the filling factor is the ratio of the spacer area in contact with the layer of uniform thickness to the total plate area in contact with the layer of uniform thickness.

AA29. The device of any prior embodiment, wherein for a flexible plate, the thickness of the flexible plate times the Young's modulus of the flexible plate is in the range 60 to 750 GPa-um.

AA30. The device of any prior embodiment, wherein for a flexible plate, the fourth power of the inter-spacer-distance (ISD) divided by the thickness of the flexible plate (h) and the Young's modulus (E) of the flexible plate, $ISD4/(hE)$, is equal to or less than 106 um3/GPa, AA31. The device of any prior paragraph, wherein one or both plates comprises a location marker, either on a surface of or inside the plate, that provides information of a location of the plate.

AA32. The device of any prior paragraph, wherein one or both plates comprises a scale marker, either on a surface of or inside the plate, that provides information of a lateral dimension of a structure of the sample and/or the plate.

AA33. The device of any prior embodiment, wherein one or both plates comprises an imaging marker, either on surface of or inside the plate, that assists an imaging of the sample.

AA34. The device of any prior embodiment, wherein the spacers function as a location marker, a scale marker, an imaging marker, or any combination of thereof.

AA35. The device of any prior embodiment, wherein the average thickness of the layer of uniform thickness is about equal to a minimum dimension of an analyte in the sample.

AA36. The device of any prior embodiment, wherein the inter-spacer distance is in the range of 1 µm to 50 µm.

AA37. The device of any prior embodiment, wherein the inter-spacer distance is in the range of 50 µm to 120 µm.

AA38. The device of any prior embodiment, wherein the inter-spacer distance is in the range of 120 µm to 200 µm.

AA39. The device of any prior embodiment, wherein the inter-spacer distance is substantially periodic.

AA40. The device of any prior embodiment, wherein the inter-spacer distance is aperiodic.

AA41. The device of any prior embodiment, wherein the spacers are pillars with a cross-sectional shape selected from round, polygonal, circular, square, rectangular, oval, elliptical, or any combination of the same.

AA42. The device of any prior embodiment, wherein the spacers have a pillar shape and have a substantially flat top surface, wherein, for each spacer, the ratio of the lateral dimension of the spacer to its height is at least 1.

AA43. The device of any prior embodiment, wherein each spacer has a ratio of the lateral dimension of the spacer to its height at least 1.

AA44. The device of any prior embodiment, wherein the minimum lateral dimension of spacer is less than or substantially equal to the minimum dimension of an analyte in the sample.

AA45. The device of any prior embodiment, wherein the minimum lateral dimension of spacer is in the range of 0.5 um to 100 um.

AA46. The device of any prior embodiment, wherein the minimum lateral dimension of spacer is in the range of 0.5 um to 10 um.

AA47. The device of any prior embodiment, wherein the spacers have a density of at least $100/mm^2$.

AA48. The device of any prior embodiment, wherein the spacers have a density of at least $1000/mm^2$.

AA49. The device of any prior embodiment, wherein at least one of the plates is transparent.

AA50. The device of any prior embodiment, wherein at least one of the plates is made from a flexible polymer.

AA51. The device of any prior embodiment, wherein, for a pressure that compresses the plates, the spacers are not compressible and/or, independently, only one of the plates is flexible.

AA52. The device of any of any prior embodiment, wherein the flexible plate has a thickness in the range of 10 µm to 200 µm.

AA53. The device of any prior embodiment, wherein the variation is less than 30%.

AA54. The device of any prior embodiment, wherein the variation is less than 10%.

AA55. The device of any prior embodiment, wherein the variation is less than 5%.

AA56. The device of any prior embodiment, wherein the first and second plates are connected and are configured to be changed from the open configuration to the closed configuration by folding the plates.

AA57. The device of any prior embodiment, wherein the first and second plates are connected by a hinge and are configured to be changed from the open configuration to the closed configuration by folding the plates along the hinge.

AA58. The device of any prior embodiment, wherein the first and second plates are connected by a hinge that is a separate material to the plates, and are configured to be changed from the open configuration to the closed configuration by folding the plates along the hinge.

AA59. The device of any prior embodiment, wherein the first and second plates are made in a single piece of material and are configured to be changed from the open configuration to the closed configuration by folding the plates.

AA60. The device of any prior embodiment, wherein the layer of uniform thickness sample is uniform over a lateral area that is at least 100 $um^2$.

AA61. The device of any prior embodiment, wherein the layer of uniform thickness sample is uniform over a lateral area that is at least 1 $mm^2$.

AA62. The device of any prior embodiment, wherein the device is configured to analyze the sample in 60 seconds or less.

AA63. The device of any prior embodiment, wherein at the closed configuration, the final sample thickness device is configured to analyze the sample in 60 seconds or less.

AA64. The device of any prior embodiment, wherein the device further comprises, on one or both of the plates, one or a plurality of amplification sites that are each capable of amplifying a signal from the analyte or a label of the analyte when the analyte or label is within 500 nm from an amplification site.

AA65. The device of any prior embodiment, wherein at the closed configuration, the final sample thickness device is configured to analyze the sample in 10 seconds or less.

AA66. The device of any prior embodiment, wherein the dry binding site comprises a capture agent.

AA67. The device of any prior embodiment, wherein the dry binding site comprises an antibody or nucleic acid.

AA68. The device of any prior embodiment, wherein the releasable dry reagent is a labeled reagent.

AA69. The device of any prior embodiment, wherein the releasable dry reagent is a fluorescently-labeled reagent.

AA70. The device of any prior embodiment, wherein the releasable dry reagent is a fluorescently-labeled antibody.

AA71. The device of any prior embodiment, wherein the first plate further comprises, on its surface, a first predetermined assay site and a second predetermined assay site, wherein the distance between the edges of the assay site is substantially larger than the thickness of the uniform thickness layer when the plates are in the closed position, wherein at least a part of the uniform thickness layer is over the predetermined assay sites, and wherein the sample has one or a plurality of analytes that are capable of diffusing in the sample.

AA72. The device of any prior embodiment, wherein the first plate has, on its surface, at least three analyte assay sites, and the distance between the edges of any two neighboring assay sites is substantially larger than the thickness of the uniform thickness layer when the plates are in the closed position, wherein at least a part of the uniform thickness layer is over the assay sites, and wherein the sample has one or a plurality of analytes that are capable of diffusing in the sample.

AA73. The device of any prior embodiment, wherein the first plate has, on its surface, at least two neighboring analyte assay sites that are not separated by a distance that is substantially larger than the thickness of the uniform thickness layer when the plates are in the closed position, wherein at least a part of the uniform thickness layer is over the assay sites, and wherein the sample has one or a plurality of analytes that are capable of diffusing in the sample.

AA74. The device of any prior embodiment, wherein the releasable dry reagent is a cell stain.

AA75. The device of any prior embodiment, wherein the device further comprises a detector that is an optical detector for detecting an optical signal.

AA76. The device of any prior embodiment, wherein the device further comprises a detector that is an electrical detector for detecting an electric signal.

AA77. The device of any prior embodiment, wherein the device comprises discrete spacers that are not fixed to any of the plates, wherein at the closed configuration, the discrete spacers are between the inner surfaces of the two plates, and the thickness of the sample is confined by the inner surfaces of the two plates, and regulated by the discrete spacers and the plates.

AA78. The device of any prior embodiment, wherein the device further comprises a binding site that has a chemical sensor that is made from a material selected from the group consisting of: silicon nanowire (Si NW); single-walled carbon nanotubes (SWCNT); random networks of carbon nanotubes (RN-CNTs); molecularly capped metal nanoparticles (MCNPs); metal oxide nanoparticles (MONPs); and chemically sensitive field-effect transistors (CHEM-FETs).

BB1. A system for rapidly analyzing a vapor condensation sample using a mobile phone comprising:
(a) a device of any prior AA embodiment;
(b) a mobile communication device comprising:
i. one or a plurality of cameras for the detecting and/or imaging the vapor condensate sample; and
ii. electronics, signal processors, hardware and software for receiving and/or processing the detected signal and/or the image of the vapor condensate sample and for remote communication.

BB2. The system of any prior BB embodiment, wherein the system further comprise a light source from either the mobile communication device or an external source.

BB3. The system of any prior BB embodiment, wherein one of the plates has a binding site that binds an analyte, wherein at least part of the uniform sample thickness layer is over the binding site, and is substantially less than the average lateral linear dimension of the binding site.

BB4. The system of any prior BB embodiment, further comprising:
(d) a housing configured to hold the sample and to be mounted to the mobile communication device.

BB5. The system of any prior BB embodiment, wherein the housing comprises optics for facilitating the imaging and/or signal processing of the sample by the mobile communication device, and a mount configured to hold the optics on the mobile communication device.

BB6. The system of any prior BB embodiment, wherein an element of the optics in the housing is movable relative to the housing.

BB7. The system of any prior BB embodiment, wherein the mobile communication device is configured to communicate test results to a medical professional, a medical facility or an insurance company.

BB8. The system of any prior BB embodiment, wherein the mobile communication device is further configured to communicate information on the test and the subject with the medical professional, medical facility or insurance company.

BB9. The system of any prior BB embodiment, wherein the mobile communication device is further configured to communicate information of the test to a cloud network, and the cloud network process the information to refine the test results.

BB10. The system of any prior BB embodiment, wherein the mobile communication device is further configured to communicate information of the test and the subject to a cloud network, the cloud network process the information to refine the test results, and the refined test results will send back the subject.

BB11. The system of any prior BB embodiment, wherein the mobile communication device is configured to receive a prescription, diagnosis or a recommendation from a medical professional.

BB12. The system of any prior BB embodiment, wherein the mobile communication device is configured with hardware and software to:
(a) capture an image of the sample;
(b) analyze a test location and a control location in in image; and
(c) compare a value obtained from analysis of the test location to a threshold value that characterizes the rapid diagnostic test.

BB13. The system of any prior BB embodiment, wherein at least one of the plates comprises a storage site in which assay reagents are stored.

BB14. The system of any prior BB embodiment, at least one of the cameras reads a signal from the CROF device.

BB15. The system of any prior BB embodiment, wherein the mobile communication device communicates with the remote location via a wifi or cellular network.

BB16. The system of any prior BB embodiment, wherein the mobile communication device is a mobile phone.

CC1. A method for rapidly analyzing an analyte in a sample using a mobile phone, comprising:
(a) depositing a sample on the device of any prior BB embodiment;
(b) assaying an analyte in the sample deposited on the device to generate a result; and
(c) communicating the result from the mobile communication device to a location remote from the mobile communication device.

CC2. The method of any prior CC embodiment, wherein the analyte comprises a molecule (e.g., a protein, peptides, DNA, RNA, nucleic acid, or other molecule), cells, tissues, viruses, and nanoparticles with different shapes.

CC3. The method of any prior CC embodiment, wherein the analyte comprises white blood cell, red blood cell and platelets.

CC4. The method of any prior CC embodiment, wherein the method comprises:
analyzing the results at the remote location to provide an analyzed result; and communicating the analyzed result from the remote location to the mobile communication device.

CC5. The method of any prior CC embodiment, wherein the analysis is done by a medical professional at a remote location.

CC6. The method of any prior CC embodiment, wherein the mobile communication device receives a prescription, diagnosis or a recommendation from a medical professional at a remote location.

CC7. The method of any prior CC embodiment, wherein the thickness of the at least a part of VC sample at the closed configuration is larger than the thickness of VC sample deposited on the collection plate at an open configuration.

CC8. The method of any prior CC embodiment, wherein the thickness of the at least a part of VC sample at the closed configuration is less than the thickness of VC sample deposited on the collection plate at an open configuration.

CC9. The method of any prior CC paragraph, wherein the assaying step comprises detecting an analyte in the sample.
CC10. The method of any prior CC paragraph, wherein the analyte is a biomarker.
CC11. The method of any prior CC embodiment, wherein the analyte is a protein, nucleic acid, cell, or metabolite.
CC12. The method of any prior CC embodiment, wherein the assay done in step (b) is a binding assay or a biochemical assay.
DD1. A method for analyzing an analyte in a vapor condensate sample comprising: obtaining a device of any prior device claim;
depositing the vapor condensate sample onto one or both pates of the device;
placing the plates in a closed configuration and applying an external force over at least part of the plates; and
analyzing the analytes in the layer of uniform thickness while the plates are the closed configuration.
DD2. The method of any prior DD embodiment, wherein the method comprises:
  (a) obtaining a sample;
  (b) obtaining a first and second plates that are movable relative to each other into different configurations, wherein each plate has a sample contact surface that is substantially planar, one or both plates are flexible, and one or both of the plates comprise spacers that are fixed with a respective sample contacting surface, and wherein the spacers have:
    i. a predetermined substantially uniform height,
    ii. a shape of pillar with substantially uniform cross-section and a flat top surface;
    iii. a ratio of the width to the height equal or larger than one;
    iv. a predetermined constant inter-spacer distance that is in the range of 10 $\mu$m to 200 $\mu$m;
    v. a filling factor of equal to 1% or larger;
  (c) depositing the sample on one or both of the plates when the plates are configured in an open configuration, wherein the open configuration is a configuration in which the two plates are either partially or completely separated apart and the spacing between the plates is not regulated by the spacers;
  (d), after (c), using the two plates to compress at least part of the sample into a layer of substantially uniform thickness that is confined by the sample contact surfaces of the plates, wherein the uniform thickness of the layer is regulated by the spacers and the plates, and has an average value equal to or less than 30 um with a variation of less than 10%, wherein the compressing comprises:
    bringing the two plates together; and
    conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and
  (e) analyzing the in the layer of uniform thickness while the plates are the closed configuration;
  wherein the filling factor is the ratio of the spacer contact area to the total plate area; wherein a conformable pressing is a method that makes the pressure applied over an area is substantially constant regardless the shape variation of the outer surfaces of the plates; and
  wherein the parallel pressing applies the pressures on the intended area at the same time, and a sequential pressing applies the pressure on a part of the intended area and gradually move to other area.
DD3. The method of any prior DD embodiment, wherein the method comprises:
  removing the external force after the plates are in the closed configuration; and imaging the analytes in the layer of uniform thickness while the plates are the closed configuration; and
  counting a number of analytes or the labels in an area of the image.
DD4. The method of any prior DD embodiment, wherein the method comprises removing the external force after the plates are in the closed configuration; and measuring optical signal in the layer of uniform thickness while the plates are the closed configuration.
DD5. The method of any prior DD embodiment, wherein the inter-spacer distance is in the range of 20 $\mu$m to 200 $\mu$m.
DD6. The method of any prior DD embodiment, wherein the inter-spacer distance is in the range of 5 $\mu$m to 20 $\mu$m.
DD7. The method of any prior DD embodiment, wherein a product of the filling factor and the Young's modulus of the spacer is 2 MPa or larger.
DDB. The method of any prior DD embodiment, the surface variation is less than 50 nm.
DD9. The method of any prior DD embodiment, further comprising a step of calculating the concentration of an analyte in the relevant volume of sample, wherein the calculation is based on the relevant sample volume defined by the predetermined area of the storage site, the uniform sample thickness at the closed configuration, and the amount of target entity detected.
DD10. The method of any prior DD embodiment, wherein the analyzing step comprise counting the ananlyte in the sample.
DD11. The method of any prior DD embodiment, wherein the imaging and counting is done by:
  i. illuminating the cells in the layer of uniform thickness;
  ii. taking one or more images of the cells using a CCD or CMOS sensor;
  iii. identifying cells in the image using a computer; and
  iv. counting a number of cells in an area of the image.
DD12. The method of any prior DD embodiment, wherein the external force is provided by human hand.
DD13. The method of any prior DD embodiment, wherein it future comprises a dry reagent coated on one or both plates.
DD14. The method of any prior DD embodiment, wherein the layer of uniform thickness sample has a thickness uniformity of up to +/−5%.
DD15. The method of any prior DD embodiment, wherein the spacers are pillars with a cross-sectional shape selected from round, polygonal, circular, square, rectangular, oval, elliptical, or any combination of the same.
DD16. The method of any prior DD embodiment, wherein the spacing between the spacers is approximately the minimum dimension of an analyte.
EE1. The method of any prior CC or DD embodiment, wherein one or both plate sample contact surfaces comprises one or a plurality of amplification sites that are each capable of amplifying a signal from the analyte or a label of the analyte when the analyte or label is within 500 nm from an amplification site.
EE2. The method of any prior CC or DD embodiment, wherein the sample is exhale breath condensate.

EE3. The method of any prior CC or DD embodiment, wherein the sample is a vapor from a biological sample, an environmental sample, a chemical sample, or clinical sample.

EE4. The method of any prior CC or DD embodiment, wherein the analyte comprises a molecule (e.g., a protein, peptides, DNA, RNA, nucleic acid, or other molecules), cells, tissues, viruses, and nanoparticles with different shapes.

EE5. The method of any prior CC or DD embodiment, wherein the analyte comprises volatile organic compounds (VOCs).

EE6. The method of any prior CC or DD embodiment, wherein the analyte comprises nitrogen, oxygen, CO2, H2O, and inert gases.

EE7. The method of any prior CC or DD embodiment, wherein the analyte is stained.

EE8. The method of any prior CC or DD embodiment, wherein on one of the sample surface, it further comprises an enclosure-spacer that encloses a partial or entire VC samples deposited on the collection plate.

EE9. The method of any prior CC or DD embodiment, wherein the highly uniform thickness has a value equal to or less than 0.5 um.

EE10. The method of any prior CC or DD embodiment, wherein the highly uniform thickness has a value in the range of 0.5 um to 1 um.

EE11. The method of any prior CC or DD embodiment, wherein the highly uniform thickness has a value in the range of 1 um to 2 um.

EE12. The method of any prior CC or DD embodiment, wherein the highly uniform thickness has a value in the range of 2 um to 10 um.

EE13. The method of any prior CC or DD embodiment, wherein the highly uniform thickness has a value in the range of 10 um to 20 um.

EE14. The method of any prior CC or DD embodiment, wherein the highly uniform thickness has a value in the range of 20 um to 30 um.

OTHER EMBODIMENTS

The present invention includes a variety of embodiments, which can be combined in multiple ways as long as the various components do not contradict one another. The embodiments should be regarded as a single invention file: each filing has other filing as the references and is also referenced in its entirety and for all purpose, rather than as a discrete independent. These embodiments include not only the disclosures in the current file, but also the documents that are herein referenced, incorporated, or to which priority is claimed.

(1) Definitions

The terms used in describing the devices, systems, and methods herein disclosed are defined in the current application, or in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/426,065, which was filed on Feb. 8, 2017, U.S. Provisional Application No. 62/456,504, which was filed on Feb. 8, 2017, all of which applications are incorporated herein in their entireties for all purposes.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF card) that regulate the spacing between the plates. The term "X-plate" refers to one of the two plates in a CROF card, wherein the spacers are fixed to this plate. More descriptions of the COF Card, CROF Card, and X-plate are given in the provisional application Ser. No. 62/456,065, filed on Feb. 7, 2017, which is incorporated herein in its entirety for all purposes.

(2) Q-Card, Spacer and Uniform Sample Thickness

The devices, systems, and methods herein disclosed can include or use Q-cards, spacers, and uniform sample thickness embodiments for sample detection, analysis, and quantification. In some embodiments, the Q-card comprises spacers, which help to render at least part of the sample into a layer of high uniformity. The structure, material, function, variation and dimension of the spacers, as well as the uniformity of the spacers and the sample layer, are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/426,065, which was filed on Feb. 8, 2017, U.S. Provisional Application No. 62/456,504, which was filed on Feb. 8, 2017, all of which applications are incorporated herein in their entireties for all purposes.

(3) Hinges, Opening Notches, Recessed Edge and Sliders

The devices, systems, and methods herein disclosed can include or use Q-cards for sample detection, analysis, and quantification. In some embodiments, the Q-card comprises hinges, notches, recesses, and sliders, which help to facilitate the manipulation of the Q card and the measurement of the samples. The structure, material, function, variation and dimension of the hinges, notches, recesses, and sliders are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/426,065, which was filed on Feb. 8, 2017, U.S. Provisional Application No. 62/456,504, which was filed on Feb. 8, 2017, all of which applications are incorporated herein in their entireties for all purposes.

(4) Q-Card, Sliders, and Smartphone Detection System

The devices, systems, and methods herein disclosed can include or use Q-cards for sample detection, analysis, and quantification. In some embodiments, the Q-cards are used together with sliders that allow the card to be read by a smartphone detection system. The structure, material, function, variation, dimension and connection of the Q-card, the sliders, and the smartphone detection system are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/426,065, which was filed on Feb. 8, 2017, U.S. Provisional Application No. 62/456,504, which was filed on Feb. 8, 2017, all of which applications are incorporated herein in their entireties for all purposes.

In some embodiments of QMAX, the sample contact area of one or both of the plates comprises a compressed open flow monitoring surface structures (MSS) that are configured to monitoring how much flow has occurred after COF. For examples, the MSS comprises, in some embodiments, shallow square array, which will cause friction to the components (e.g. blood cells in a blood) in a sample. By checking the distributions of some components of a sample, one can obtain information related to a flow, under a COF, of the sample and its components.

The depth of the MSS can be $1/1000$, $1/100$, $1/100$, $1/5$, $1/2$ of the spacer height or in a range of any two values, and in either protrusion or well form.

(5) Detection Methods

The devices, systems, and methods herein disclosed can include or be used in various types of detection methods. The detection methods are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/426,065, which was filed on Feb. 8, 2017, U.S. Provisional Application No. 62/456,504, which was filed on Feb. 8, 2017, all of which applications are incorporated herein in their entireties for all purposes.

(6) Labels

The devices, systems, and methods herein disclosed can employ various types of labels that are used for analytes detection. The labels are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/426,065, which was filed on Feb. 8, 2017, U.S. Provisional Application No. 62/456,504, which was filed on Feb. 8, 2017, all of which applications are incorporated herein in their entireties for all purposes.

(7) Analytes

The devices, systems, and methods herein disclosed can be applied to manipulation and detection of various types of analytes (including biomarkers). The analytes and are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/426,065, which was filed on Feb. 8, 2017, U.S. Provisional Application No. 62/456,504, which was filed on Feb. 8, 2017, all of which applications are incorporated herein in their entireties for all purposes.

(8) Applications (Field and Samples)

The devices, systems, and methods herein disclosed can be used for various applications (fields and samples). The applications are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/426,065, which was filed on Feb. 8, 2017, U.S. Provisional Application No. 62/456,504, which was filed on Feb. 8, 2017, all of which applications are incorporated herein in their entireties for all purposes.

(9) Cloud

The devices, systems, and methods herein disclosed can employ cloud technology for data transfer, storage, and/or analysis. The related cloud technologies are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/426,065, which was filed on Feb. 8, 2017, U.S. Provisional Application No. 62/456,504, which was filed on Feb. 8, 2017, all of which applications are incorporated herein in their entireties for all purposes.

ADDITIONAL NOTES

Further examples of inventive subject matter according to the present disclosure are described in the following enumerated paragraphs.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function may additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity may optionally be present other than the entity specifically identified by the "and/or" clause, whether related or unrelated to those entities specifically identified.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

The invention claimed is:

1. A method for collecting and analyzing an analyte in a vapor sample, comprising:
   (a) having a device comprising a collection plate, a cover plate, and at least one reagent, wherein:
      (i) the two plates are movable relative to each other into different configurations, including an open configuration and a closed configuration;
      (ii) one or both of the two plates are flexible;
      (iii) each of the two plates has, on its inner respective surface, a sample contact area for contacting a vapor condensate (VC) sample that contains or is suspected of containing an analyte; and
      (iv) one or both sample contact areas have the at least one reagent;
   wherein in the open configuration, the two plates are either completely or partially separated apart, and the VC sample is deposited on one or both of the plates;
   wherein in the closed configuration, at least a part of the VC sample is between the two plates and in contact with the two plates, and has a thickness that (a) is regulated by the two sample contact surfaces of the plates, and (b) is equal to or less than 30 micrometers;
   (b) depositing, in the open configuration, the vapor sample on one or both of the plates by directly condensing a vapor of the VC sample on one plate or the two plates;
   (c) bringing, after step (b), the two plates into the closed configuration; and
   (d) analyzing, after step (c), the analyte in the vapor sample to generate a result,
      wherein a covering time delay is 120 seconds or less, and the covering time delay is the time delay between the end of step (b) depositing the vapor sample and the end of the step (c) bringing the two plates into the closed configuration.

2. The method of claim 1, further comprising wherein the covering time delay is 60 seconds or less.

3. The method of claim 1, wherein the analyte comprises a molecule (e.g., a protein, peptides, DNA, RNA, nucleic acid, or other molecule), cells, tissues, viruses, and nanoparticles with different shapes.

4. The method of claim 1, wherein the method uses a mobile communication device, and wherein the method comprises:
   analyzing the results at the remote location, from the site that generates the result, to provide a remotely analyzed result; and
   communicating the remotely analyzed result from the remote location to the mobile communication device.

5. The method of claim 1, wherein the step (d) of analyzing the sample using a device comprising a mobile communication device comprises:
   one or a plurality of cameras for the detecting and/or imaging the vapor condensate sample in the device; and
   electronics, signal processors, hardware and software for receiving and/or processing a detected signal and/or an image of the vapor condensate sample, and for remote communication.

6. The method of claim 1, The method of claim 1, wherein step (d) of analyzing the sample using a device comprising a camera that images the sample.

7. The method of claim 1, wherein the thickness of the sample is regulated by the two sample contact surfaces of the plates without using spacers.

8. The method of claim 1, wherein the analyte is a breath biomarker.

9. The method of claim 1, wherein the analyte comprises a molecule, cells, tissues, viruses, or nanoparticles with different shapes, or a combination thereof, wherein the molecule comprises a protein, peptides, DNA, RNA, or nucleic acid.

10. The method of claim 1, wherein the analyte comprises a volatile organic compound (VOC), nitrogen, oxygen, $CO_2$, $H_2O$, or inert gases.

11. The method of claim 1, wherein the reagent is a staining reagent.

12. The method of claim 1, wherein the device further comprises a labeled nucleic acid on the plate, the analyte is nucleic acid, and the nucleic acid analyte hybridizes with the labeled nucleic acid.

13. The method of claim 1, wherein the reagent is a dye, a bead, a quantum dot, or a fluorescently-labeled antibody.

14. The method of claim 1, wherein the reagent is selected from the group consisting of an antibody, a nucleic acid, cell stain, a dye, a protein, a releasable dry reagent, a labeled reagent, a fluorescently-labeled reagent, a dye, a bead, a quantum dot, the capture agent, detection agent, and blocking agent, light signal enhancers, light signal quenchers, and a fluorescently-labeled antibody.

15. The method of claim 1, wherein the reagent comprises the detectable label selected from the group consisting of a fluorescent label, a colorimetric label, a chemiluminescent label, an enzyme-linked reagent, a multicolor reagent, and an avidin-streptavidin associated detection reagent.

16. The method of claim 1, further comprising a plurality of spacers that regulates to the spacer between the two plates, wherein for a flexible plate, a fourth power of the inter-spacer distance (ISD) divided by a thickness of the flexible plate (h) and a Young's modulus (E) of the flexible plate, $ISD^4/(hE)$, is equal to or less than $10^6$ um.sup.3/GPa, and wherein the thickness of the flexible plate times a Young's modulus of the flexible plate is in the range of 60 to 750 GPa-um.

17. The method of claim 1, wherein the sample thickness at the closed configuration is between 0.5 um to 10 um.

18. The method of claim 1, wherein the step (d) of the analyzing sample comprises a use of a device comprising a camera and communication hardware and software that can take an image using the camera, manipulate the image, and communicate data to a remote place.

19. The method of claim 1, wherein the step (d) of the analyzing sample comprises:
(i) taking an image of the sample, (ii) sending the image to a remote location, (iii) analyzing the results at the remote location to provide an analyzed result; and (iv) communicating the analyzed result from the remote location to the mobile communication device.

20. The method of claim 1, wherein the step (d) of the analyzing sample comprises:
(i) assaying an analyte in the sample deposited on the device to generate a result aznt location that sample is collected; and (ii) communicating the result from the mobile communication device to a location remote from the mobile communication device.

* * * * *